(12) United States Patent
He et al.

(10) Patent No.: US 12,220,279 B2
(45) Date of Patent: Feb. 11, 2025

(54) METHOD, SYSTEM, AND STORAGE MEDIUM FOR ULTRASONIC IMAGING

(71) Applicant: WUHAN UNITED IMAGING HEALTHCARE CO., LTD., Hubei (CN)

(72) Inventors: Cheng He, Wuhan (CN); Oliver Heid, Erlangen (DE)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 239 days.

(21) Appl. No.: 17/810,338

(22) Filed: Jun. 30, 2022

(65) Prior Publication Data

US 2022/0338839 A1 Oct. 27, 2022

Related U.S. Application Data

(63) Continuation of application No. PCT/CN2021/131585, filed on Nov. 18, 2021.

(30) Foreign Application Priority Data

Nov. 18, 2020 (CN) .......................... 202011293102.9
Dec. 29, 2020 (WO) ................ PCT/CN2020/140621
Oct. 22, 2021 (CN) .......................... 202111232861.9

(51) Int. Cl.
  *A61B 8/00* (2006.01)
(52) U.S. Cl.
  CPC ............ *A61B 8/461* (2013.01); *A61B 8/4444* (2013.01); *A61B 8/5207* (2013.01); *A61B 8/565* (2013.01); *A61B 8/58* (2013.01)
(58) Field of Classification Search
  CPC ..... A61B 8/461; A61B 8/4444; A61B 8/5207; A61B 8/565; A61B 8/58
  See application file for complete search history.

(56) References Cited

U.S. PATENT DOCUMENTS 3,693,415 A * 9/1972 Whittington ............. A61B 8/12
                                                          367/105
5,462,057 A 10/1995 Hunt et al.
(Continued)

FOREIGN PATENT DOCUMENTS

CN     1788685 A    6/2006
CN   101209211 A    7/2008
(Continued)

OTHER PUBLICATIONS

Hou, Shanshan, Study on the Method of Partial Discharge Ultrasonic Array Sensors' Sparse Design, Chinese Master's Theses Full-text Database Engineering Science and Technology Series II, 2015, 66 pages.
(Continued)

*Primary Examiner* — Dixomara Vargas
(74) *Attorney, Agent, or Firm* — METIS IP LLC

(57) ABSTRACT

The present disclosure discloses an ultrasonic imaging method. The ultrasonic imaging method may include: obtaining emitting instructions for emitting a plurality of ultrasonic waves, gaining instructions, receiving instructions, and idle instructions relating to the plurality of ultrasonic waves, and storing the emitting instructions, the receiving instructions, the gaining instructions, and the idle instructions in a ring buffer; obtaining the emitting instructions from the ring buffer, and emitting the plurality of ultrasonic waves based on the emitting instructions; obtaining a gaining instruction and a receiving instruction corresponding to each emission of the plurality of ultrasonic waves from the ring buffer, and obtaining at least one enhanced echo signal based on the gaining instructions and the receiving instructions; and obtaining the idle instructions from the ring buffer, and processing the at least one
(Continued)

enhanced echo signal based on the idle instructions to obtain a target ultrasonic image.

20 Claims, 19 Drawing Sheets

(56) References Cited

U.S. PATENT DOCUMENTS

| | | | |
|---|---|---|---|
| 5,549,002 A * | 8/1996 | Howard | G01S 15/8997 |
| | | | 73/620 |
| 5,676,149 A * | 10/1997 | Yao | B06B 1/0207 |
| | | | 600/437 |
| 6,038,925 A * | 3/2000 | Ohtani | H02K 33/12 |
| | | | 73/598 |
| 6,080,107 A | 6/2000 | McKee | |
| 6,234,025 B1 * | 5/2001 | Gieske | G10K 11/30 |
| | | | 73/629 |
| 6,629,929 B1 | 10/2003 | Jago et al. | |
| 7,255,678 B2 | 8/2007 | Mehi et al. | |
| 8,037,767 B2 | 10/2011 | Kim et al. | |
| 9,116,229 B2 | 8/2015 | Shifrin | |
| 10,466,354 B2 | 11/2019 | Ramamurthy | |
| 10,675,000 B2 | 6/2020 | Specht et al. | |
| 10,979,018 B1 * | 4/2021 | Siddiqui | H03H 9/14547 |
| 2005/0187494 A1 | 8/2005 | He et al. | |
| 2008/0125660 A1 | 5/2008 | Yao et al. | |
| 2008/0242992 A1 | 10/2008 | Criton | |
| 2009/0054780 A1 | 2/2009 | Yang et al. | |
| 2009/0062648 A1 * | 3/2009 | Derby, Jr. | A61B 8/00 |
| | | | 600/443 |
| 2009/0088638 A1 | 4/2009 | Sato et al. | |
| 2009/0088644 A1 | 4/2009 | Yao et al. | |
| 2010/0268082 A1 | 10/2010 | McLaughlin et al. | |
| 2010/0321515 A1 | 12/2010 | Imamura | |
| 2011/0030479 A1 * | 2/2011 | Murai | G01N 29/223 |
| | | | 73/632 |
| 2011/0102261 A1 | 5/2011 | Egri et al. | |
| 2011/0178441 A1 | 7/2011 | Tyler | |
| 2011/0319793 A1 | 12/2011 | Hynynen | |
| 2012/0071746 A1 | 3/2012 | Vortman et al. | |
| 2012/0143059 A1 | 6/2012 | Magee | |
| 2012/0232396 A1 | 9/2012 | Tanabe | |
| 2012/0232803 A1 | 9/2012 | Viola et al. | |
| 2012/0283568 A1 | 11/2012 | Loftman et al. | |
| 2013/0046168 A1 * | 2/2013 | Sui | A61B 8/0891 |
| | | | 600/407 |
| 2014/0051984 A1 | 2/2014 | Berger et al. | |
| 2016/0278742 A1 | 9/2016 | Tsushima | |
| 2016/0338676 A1 | 11/2016 | Berger et al. | |
| 2017/0336500 A1 | 11/2017 | Luo et al. | |
| 2018/0003819 A1 | 1/2018 | Koptenko | |
| 2018/0085092 A1 | 3/2018 | Lee et al. | |
| 2018/0166063 A1 | 6/2018 | Long et al. | |
| 2018/0177491 A1 * | 6/2018 | Hynynen | A61B 8/0808 |
| 2018/0296190 A1 * | 10/2018 | Susumu | A61B 8/5269 |
| 2018/0333139 A1 | 11/2018 | Misono | |
| 2018/0360420 A1 * | 12/2018 | Vortman | A61N 7/02 |
| 2018/0367126 A1 | 12/2018 | Petersen et al. | |
| 2019/0099158 A1 | 4/2019 | Ryu et al. | |
| 2019/0133556 A1 | 5/2019 | Koptenko | |
| 2020/0033471 A1 * | 1/2020 | Kim | G01S 15/8906 |
| 2020/0108412 A1 * | 4/2020 | Greenberg | G10K 11/346 |
| 2020/0268356 A1 | 8/2020 | Li | |
| 2020/0337676 A1 | 10/2020 | Kamiyama et al. | |
| 2020/0375574 A1 | 12/2020 | Ling et al. | |
| 2022/0163646 A1 | 5/2022 | Fraschini et al. | |
| 2022/0233890 A1 * | 7/2022 | Hynynen | A61B 8/4477 |

FOREIGN PATENT DOCUMENTS

| | | |
|---|---|---|
| CN | 101664321 A | 3/2010 |
| CN | 101770028 A | 7/2010 |
| CN | 101785684 A | 7/2010 |
| CN | 102247168 A | 11/2011 |
| CN | 104020462 A | 9/2014 |
| CN | 105044706 A | 11/2015 |
| CN | 105193453 A | 12/2015 |
| CN | 106063710 A | 11/2016 |
| CN | 107320129 A | 11/2017 |
| CN | 107374670 A | 11/2017 |
| CN | 108186045 A | 6/2018 |
| CN | 108198610 A | 6/2018 |
| CN | 108354627 A | 8/2018 |
| CN | 108519576 A | 9/2018 |
| CN | 108938003 A | 12/2018 |
| CN | 109975814 A | 7/2019 |
| CN | 110575201 A | 12/2019 |
| CN | 111374696 A | 7/2020 |
| CN | 111436966 A | 7/2020 |
| CN | 111631750 A | 9/2020 |
| CN | 112043379 A | 12/2020 |
| CN | 107997784 B | 1/2021 |
| CN | 112401932 A | 2/2021 |
| CN | 107789008 B | 3/2021 |
| CN | 107997783 B | 3/2021 |
| CN | 108324323 B | 3/2021 |
| DE | 3916396 A1 | 11/1990 |
| EP | 2952137 A1 | 12/2015 |
| JP | H11276477 A | 10/1999 |
| WO | 2012149489 A2 | 11/2012 |
| WO | 2020164299 A1 | 8/2020 |

OTHER PUBLICATIONS

First Office Action in Chinese Application No. 202011293102.9 mailed on Apr. 29, 2023, 22 pages.
The Extended European Search Report in European Application No. 21893990.8 mailed on Mar. 6, 2024, 11 pages.
The Extended European Search Report in European Application No. 20951282.1 mailed on Mar. 1, 2024, 8 pages.
Ji, Xiaoxing, Synthetic Aperture Ultrasonic Imaging Algorithm Based on Adaptive Beamforming, Chinese Master's Theses Full-text Database Information Technology, 2019, 80 pages.
Li, Chen, Research on Imaging Quality and Algorithm of Ultrasonic Phased Array, Chinese Master's Theses Full-text Database Information Technology, 2019, 73 pages.
International Search Report in PCT/CN2021/131585 mailed on Feb. 15, 2022, 7 pages.
Written Opinion in PCT/CN2021/131585 mailed on Feb. 15, 2022, 7 pages.
International Search Report in PCT/CN2020/140621 mailed on Aug. 16, 2021, 5 pages.
Written Opinion in PCT/CN2020/140621 mailed on Aug. 16, 2021, 4 pages.
First Office Action in Chinese Application No. 202111232861.9 mailed on Jul. 20, 2022, 15 pages.
Svetoslav Ivanov Nikolov et al., Practical Applications of Synthetic Aperture Imaging, 2010 IEEE International Ultrasonics Symposium Proceedings, 350-358, 2010.
Jørgen Arendt Jensen et al., Synthetic Aperture Ultrasound Imaging, Ultrasonics, 44: e5-e15, 2006.

* cited by examiner

700

Obtaining one or more emitting instructions for emitting a plurality of ultrasonic waves, one or more gaining instructions relating to the plurality of ultrasonic waves, one or more receiving instructions relating to the plurality of ultrasonic waves, and one or more idle instructions relating to the plurality of ultrasonic waves, and storing the one or more emitting instructions, the one or more receiving instructions, the one or more gaining instructions, and the one or more idle instructions in a ring buffer
710

Obtaining the one or more emitting instructions from the ring buffer, and emitting the plurality of ultrasonic waves based on the one or more emitting instructions
720

Obtaining a gaining instruction of the one or more gaining instructions and a receiving instruction of the one or more receiving instructions corresponding to each emission of the plurality of ultrasonic waves from the ring buffer, and obtaining at least one enhanced echo signal based on the one or more gaining instructions and the one or more receiving instructions
730

Obtaining the one or more idle instructions relating to the plurality of ultrasonic waves from the ring buffer, and processing the at least one enhanced echo signal based on the one or more idle instructions to obtain a target ultrasonic image
740

```
┌─────────────────────────────────────────────────────────────┐
│  Determining a first relative position corresponding to the each │
│  emission of the plurality of ultrasonic waves based on emission times │
│  and/or an emission order of the plurality of ultrasonic waves, to obtain │
│  a plurality of first relative positions corresponding to a plurality of │
│         emissions of the plurality of ultrasonic waves       │
│                              910                            │
└─────────────────────────────────────────────────────────────┘
                              ▼
┌─────────────────────────────────────────────────────────────┐
│  Mapping the plurality of first relative positions distributed at equal │
│   intervals to a plurality of second relative positions distributed at │
│     unequal intervals corresponding to the plurality of emissions │
│                              920                            │
└─────────────────────────────────────────────────────────────┘
                              ▼
┌─────────────────────────────────────────────────────────────┐
│  Determining an emission distance and a focus radius corresponding │
│  to each of the plurality of emissions based on an emission parameter │
│   and a second relative position corresponding to the each emission │
│                              930                            │
└─────────────────────────────────────────────────────────────┘
                              ▼
┌─────────────────────────────────────────────────────────────┐
│      Determining the focus position corresponding to the each │
│    emission based on the emission distance and the focus radius │
│      corresponding to the each of the plurality of emissions │
│                              940                            │
└─────────────────────────────────────────────────────────────┘
```

Dividing at least one portion of the pulses of the plurality of ultrasonic waves into a transmission group
1410

Compressing the transmission group into compressed data and transmitting the compressed data
1420

Decoding the compressed data to obtain the at least one portion of the pulses
1430

Determining at least one medium propagation time corresponding to at least one depth value of a target object based on one or more effective array elements corresponding to the each emission and the at least one depth value
1610

Determining at least one gain value corresponding to the at least one depth value based on an attenuation index of ultrasonic propagation, a noise value and the at least one medium propagation time
1620

FIG. 16

METHOD, SYSTEM, AND STORAGE MEDIUM FOR ULTRASONIC IMAGING

CROSS-REFERENCE TO RELATED APPLICATIONS

This application is a continuation of International Application No. PCT/CN2021/131585, filed on Nov. 18, 2021, which claims priority to Chinese Patent Application No. 202111232861.9, filed on Oct. 22, 2021, Chinese Patent Application No. 202011293102.9, filed on Nov. 18, 2020, and International Application No. PCT/CN2020/140621, filed on Dec. 29, 2020, the contents of each of which are hereby incorporated by reference.

TECHNICAL FIELD

The present disclosure relates to the field of ultrasonic technology, in particular, to a method, and a system for ultrasonic imaging.

BACKGROUND

Ultrasonic images refer to internal tissue images obtained by receiving and processing the scanning data by scanning a target object with ultrasonic waves for medical treatment or medical research. Each frame of the ultrasonic images may be obtained based on the scanning data corresponding to a plurality of ultrasonic emissions. However, in the process of obtaining each frame of the ultrasonic images, the ultrasonic imaging system needs to constantly switch in a plurality of states based on different control instructions, resulting in frequent memory allocation and release of storage devices. In addition, in the process of ultrasonic emission, the ultrasonic wave emitted from both sides of the ultrasonic probe may scatter, resulting in energy loss. In the process of ultrasonic propagation, ultrasonic wave may also scatter, so that some ultrasonic beams cannot reach the target object or a portion of the target object, resulting in energy loss and reducing the resolution of ultrasonic image.

Therefore, it is desirable to provide a method and system for ultrasonic imaging, which may improve the resolution of an ultrasonic image, image uniformity and efficiency of ultrasonic imaging.

SUMMARY

One aspect of the present disclosure may provide an ultrasonic imaging method. The ultrasonic imaging method may include: obtaining one or more emitting instructions for emitting a plurality of ultrasonic waves, one or more gaining instructions relating to the plurality of ultrasonic waves, one or more receiving instructions relating to the plurality of ultrasonic waves, and one or more idle instructions relating to the plurality of ultrasonic waves, and storing the one or more emitting instructions, the one or more receiving instructions, the one or more gaining instructions, and the one or more idle instructions in a ring buffer; obtaining the one or more emitting instructions from the ring buffer, and emitting the plurality of ultrasonic waves based on the one or more emitting instructions; obtaining a gaining instruction of the one or more gaining instructions and a receiving instruction of the one or more receiving instructions corresponding to each emission of the plurality of ultrasonic waves from the ring buffer, and obtaining at least one enhanced echo signal based on the one or more gaining instructions and the one or more receiving instructions; and obtaining the one or more idle instructions relating to the plurality of ultrasonic waves from the ring buffer, and processing the at least one enhanced echo signal based on the one or more idle instructions to obtain a target ultrasonic image.

Another aspect of the present disclosure may provide an ultrasonic imaging method. The ultrasonic imaging method may include: determining whether there is an invalid array element in an emission of an ultrasonic wave based on a radius of a transducer, an array element width and a focus position corresponding to the emission of the ultrasonic wave; in response to an existence of the invalid array element in the emission of the ultrasonic wave, determining one or more effective array elements corresponding to the emission of the ultrasonic wave based on the radius of the transducer, the array element width and the focus position corresponding to the emission of the ultrasonic wave; and in response to an absence of the invalid array element in the emission of the ultrasonic wave, determining all array elements of the transducer as the one or more effective array elements; and emitting the ultrasonic wave based on the one or more effective array elements corresponding to the emission of the ultrasonic wave.

Another aspect of the present disclosure may provide an ultrasonic imaging method. The ultrasonic imaging method may include: adaptively determining an effective aperture corresponding to an emission of an ultrasonic wave based on a radius of a transducer, an array element directivity angle and a focus position corresponding to the emission of the ultrasonic wave; emitting the ultrasonic wave to a target object based on the effective aperture corresponding to the emission of the ultrasonic wave, and receiving a corresponding echo signal; and generating a target ultrasonic image of the target object based on the echo signal.

Another aspect of the present disclosure may provide a method for emitting an ultrasonic wave. The method may include: determining a first relative position corresponding to each emission of a plurality of ultrasonic waves based on emission times and/or an emission order of the plurality of ultrasonic waves, to obtain a plurality of first relative positions corresponding to a plurality of emissions of the plurality of ultrasonic waves; mapping the plurality of first relative positions distributed at equal intervals to a plurality of second relative positions distributed at unequal intervals corresponding to the plurality of emissions; determining an emission distance and a focus radius corresponding to the each emission based on an emission parameter and a second relative position corresponding to the each emission; and determining a focus position corresponding to the each emission based on the emission distance and the focus radius corresponding to the each emission.

Another aspect of the present disclosure may provide an ultrasonic imaging system. The ultrasonic imaging system may include: an instruction acquisition module configured to obtain one or more emitting instructions for emitting a plurality of ultrasonic waves, one or more gaining instructions relating to the plurality of ultrasonic waves, one or more receiving instructions relating to the plurality of ultrasonic waves, and one or more idle instructions relating to the plurality of ultrasonic waves, and store the one or more emitting instructions, the one or more receiving instructions, the one or more gaining instructions, and the one or more idle instructions in a ring buffer; an emission module configured to obtain the one or more emitting instructions from the ring buffer, and emit the plurality of ultrasonic waves based on the one or more emitting instructions; a gain module configured to obtain a gaining instruction of the one or more gaining instructions and a receiving instruction of the one or more receiving instructions corresponding to each emission of the plurality of ultrasonic waves from the ring buffer, and obtain at least one enhanced echo signal based on the one or more gaining instructions and the one or more receiving instructions; and an imaging module configured to obtain the one or more idle instructions relating to the plurality of ultrasonic waves from the ring buffer, and process the at least one enhanced echo signal based on the one or more idle instructions to obtain a target ultrasonic image.

Another aspect of the present disclosure may provide an ultrasonic imaging system. The ultrasonic imaging system may include: an instruction acquisition module configured to: determine whether there is an invalid array element in an emission of an ultrasonic wave based on a radius of a transducer, an array element width and a focus position corresponding to the emission of the ultrasonic wave; in response to an existence of the invalid array element in the emission of the ultrasonic wave, determine one or more effective array elements corresponding to the emission of the ultrasonic wave based on the radius of the transducer, the array element width and the focus position corresponding to the emission of the ultrasonic wave; and in response to an absence of the invalid array element in the emission of the ultrasonic wave, determine all array elements of the transducer as the one or more effective array elements; and an emission module configured to: emit the ultrasonic wave based on the one or more effective array elements corresponding to the emission of the ultrasonic wave.

Another aspect of the present disclosure may provide an ultrasonic imaging system. The ultrasonic imaging system may include: an instruction acquisition module configured to adaptively determine an effective aperture corresponding to an emission of an ultrasonic wave based on a radius of a transducer, an array element directivity angle and a focus position corresponding to the emission of the ultrasonic wave; an emission module configured to emit the ultrasonic wave to a target object based on the effective aperture corresponding to the emission of the ultrasonic wave; a gain module configured to receive a corresponding echo signal; and an imaging module configured to generate a target ultrasonic image of the target object based on the echo signal.

Another aspect of the present disclosure may provide an ultrasonic imaging system. The ultrasonic imaging system may include an instruction acquisition module configured to: determine a first relative position corresponding to each emission of a plurality of ultrasonic waves based on emission times and/or an emission order of the plurality of ultrasonic waves, to obtain a plurality of first relative positions corresponding to a plurality of emissions of the plurality of ultrasonic waves; map the plurality of first relative positions distributed at equal intervals to a plurality of second relative positions distributed at unequal intervals corresponding to the plurality of emissions; determine an emission distance and a focus radius corresponding to the each emission based on an emission parameter and a second relative position corresponding to the each emission; and determine a focus position corresponding to each emission based on the emission distance and the focus radius corresponding to each of the plurality of emission.

Another aspect of the present disclosure may provide an ultrasonic imaging system. The ultrasonic imaging system may include an instruction acquisition module configured to: determine whether there is an invalid array element in an emission of an ultrasonic wave based on a radius of a transducer, an array element width and a focus position corresponding to the emission of the ultrasonic wave; a determination module configured to: in response to an existence of the invalid array element in the emission of the ultrasonic wave, determine one or more effective array elements corresponding to the emission of the ultrasonic wave based on the radius of the transducer, the array element width and the focus position corresponding to the emission of the ultrasonic wave; in response to an absence of the invalid array element in the emission of the ultrasonic wave, determine all array elements of the transducer as the one or more effective array elements; and an emission module configured to: emit the ultrasonic wave based on the one or more effective array elements corresponding to the emission of the ultrasonic wave.

Another aspect of the present disclosure may provide a non-transitory computer readable medium. The non-transitory computer readable medium may include computer instructions that, when executed by a computer, directs the computer to perform an ultrasonic imaging method.

The ultrasonic imaging method according to some embodiments of the present disclosure disclose storing the one or more emitting instructions, the one or more gaining instructions, the one or more receiving instructions and the one or more idle instructions directly in any position in the ring buffer in any order, and taking out these instructions from the ring buffer for execution based on a corresponding storage position respectively, which may avoid frequent memory allocation and release, reduce system overhead and memory fragments, and improve the operation efficiency of the system; mapping the plurality of first relative positions distributed at equal intervals to a plurality of second relative positions distributed at unequal intervals corresponding to the plurality of emissions based on a curve, and designing the focus trajectory of emitting the ultrasonic waves with dense focus on both sides based on the plurality of second relative positions distributed at unequal intervals and the curvature of the transducer, which may compensate for the low resolution of the edge of ultrasonic image caused by the energy loss on both sides of the ultrasonic probe, at the same time, the focus trajectory of emitting the ultrasonic waves with dense middle focus may be designed for the convex array ultrasonic probe, to improve the ultrasonic image resolution of the target object in the deep position; determining the effective array element (or effective aperture) based on the array element directivity may improve the influence of acoustic grating lobe and reduce the energy loss of ultrasonic in the emission process, so as to improve the image quality of ultrasonic image; dividing the pulses into transmission groups based on the transmission efficiency for compressing and transmitting, which may improve the transmission efficiency based on different bandwidth, so as to improve the efficiency of ultrasonic imaging; based on the effective aperture, the focus position and the depth value of different positions, obtaining the medium propagation time, and obtaining the corresponding gain value based on the medium propagation time, which may reduce the effective aperture, the focus position and the depth value of different positions on the intensity of the ultrasonic echo signal after gaining based on the gain value; based on the historical ultrasonic imaging data, dynamically adjusting the inter frame time, so that the inter frame time may change dynamically with changes of system performance, so as to obtain high-quality ultrasonic images.

BRIEF DESCRIPTION OF THE DRAWINGS

The present disclosure is further illustrated in terms of exemplary embodiments, and these exemplary embodiments are described in detail with reference to the drawings. These embodiments are not restrictive. In these embodiments, the same number indicates the same structure, wherein:

FIG. 7 is a flowchart illustrating an exemplary ultrasonic imaging process according to some embodiments of the present disclosure;

FIG. 9 is a flowchart illustrating an exemplary process for determining a focus position corresponding to each emission of ultrasonic waves according to some embodiments of the present disclosure;

FIG. 14 is a flowchart illustrating an exemplary process for transmitting a pulse according to some embodiments of the present disclosure;

FIG. 16 is a flowchart illustrating an exemplary process for obtaining a gain value of ultrasonic echo signal according to some embodiments of the present disclosure;

DETAILED DESCRIPTION

Figure 1:
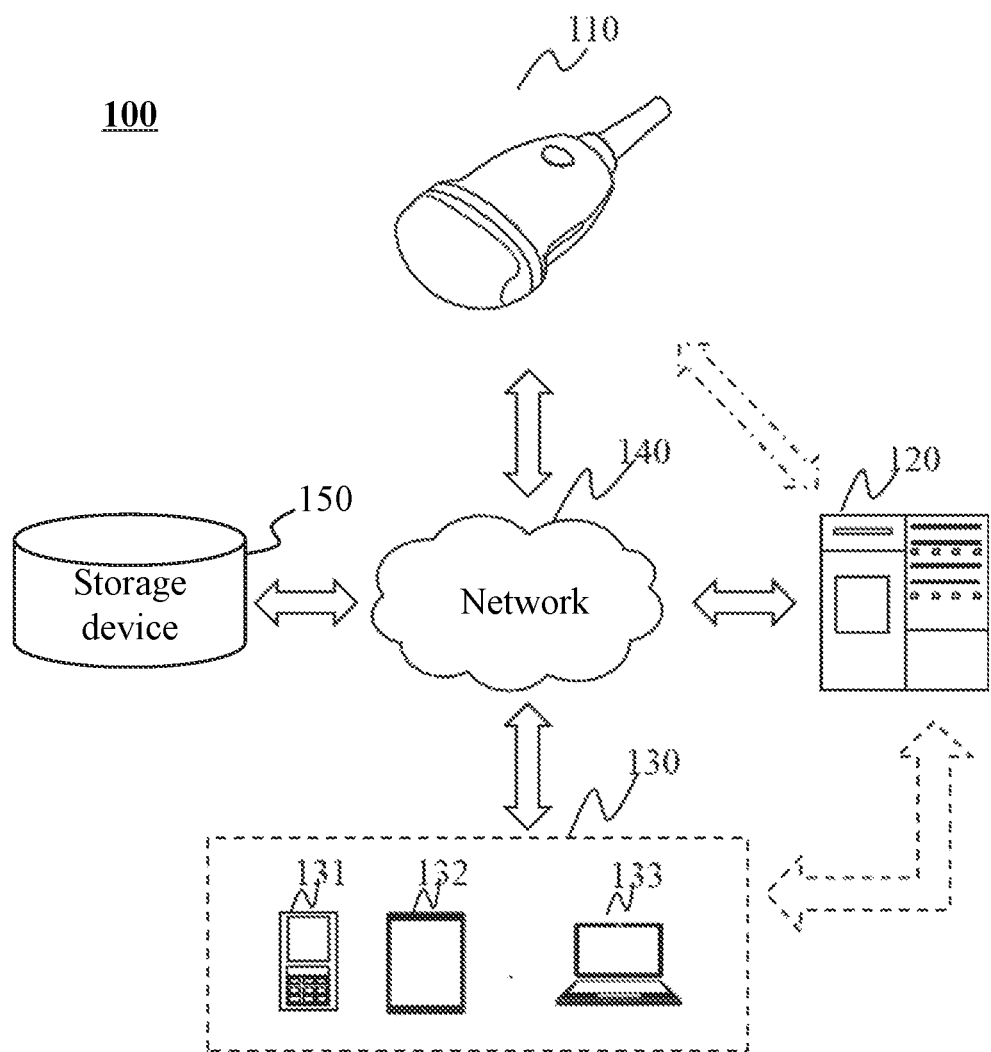
FIG. 1 is a schematic diagram illustrating an exemplary application scenario of an ultrasonic imaging system according to some embodiments of the present disclosure.

In order to illustrate the technical solutions related to the embodiments of the present disclosure, brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

It will be understood that the terms "system," "device," "unit," and/or "module" used herein are one method to distinguish different components, elements, parts, sections, or assemblies of different levels in ascending order. However, the terms may be displaced by other expressions if they may achieve the same purpose As shown in the present disclosure and claims, unless the context clearly indicates exceptions, the words "a," "an," "one," and/or "the" do not specifically refer to the singular, but may also include the plural. The terms "including" and "comprising" only suggest that the steps and elements that have been clearly identified are included, and these steps and elements do not constitute an exclusive list, and the method or device may also include other steps or elements.

The flowcharts used in the present disclosure may illustrate operations executed by the system according to embodiments in the present disclosure. It should be understood that a previous operation or a subsequent operation of the flowcharts may not be accurately implemented in order. Conversely, various operations may be performed in inverted order, or simultaneously. Moreover, other operations may be added to the flowcharts, and one or more operations may be removed from the flowcharts.

FIG. 1 is a schematic diagram illustrating an exemplary application scenario of an ultrasonic imaging system according to some embodiments of the present disclosure.

An ultrasonic imaging system 100 may determine a focus trajectory of ultrasonic emission by implementing methods and/or processes disclosed in the present disclosure, to compensate the energy loss on both sides of the ultrasonic probe and improve the resolution at edges of an ultrasonic image.

As shown in FIG. 1, the ultrasonic imaging system 100 may include an ultrasonic probe 110, a processing device 120, a terminal device 130, a network 140, and/or a storage device 150, or the like.

Components of the ultrasonic imaging system 100 may be connected in various ways. Merely by way of example, as shown in FIG. 1, the ultrasonic probe 110 may be connected to the processing device 120 through the network 140. As another example, the ultrasonic probe 110 may be directly connected to the processing device 120 (as shown by the dotted bidirectional arrow connecting the ultrasonic probe 110 and the processing device 120). As another example, the storage device 150 may be connected to the processing device 120 directly or through the network 140. As another example, the terminal device 130 may be connected to the processing device 120 directly (as shown by the dotted bidirectional arrow connecting the terminal device 130 and the processing device 120) and/or through the network 140.

The ultrasonic probe 110 may obtain scanning data. Specifically, the ultrasonic probe 110 may emit ultrasonic waves to a target object or a portion of the target object and receive reflected ultrasonic waves of the target object or a portion of the target object. In some embodiments, the ultrasonic probe 110 may include, but may not be limited to, a convex array probe, a linear array probe, a phased array probe, a high-frequency probe, or the like according to shapes. In some embodiments, the ultrasonic probe 110 may include a piezoelectric ceramic type, a single crystal type, or the like according to piezoelectric materials.

The processing device 120 may process data and/or information obtained from the ultrasonic probe 110, the terminal device 130 and/or the storage device 150. For example, the processing device 120 may determine a focus position corresponding to each emission based on the emission times and/or emission order of a plurality of ultrasonic waves. As another example, the processing device 120 may determine an effective array element corresponding to each emission based on an array element pointing angle. As another example, the processing device 120 may also update the inter frame time based on at least one set of historical ultrasonic imaging data.

Figure 2:
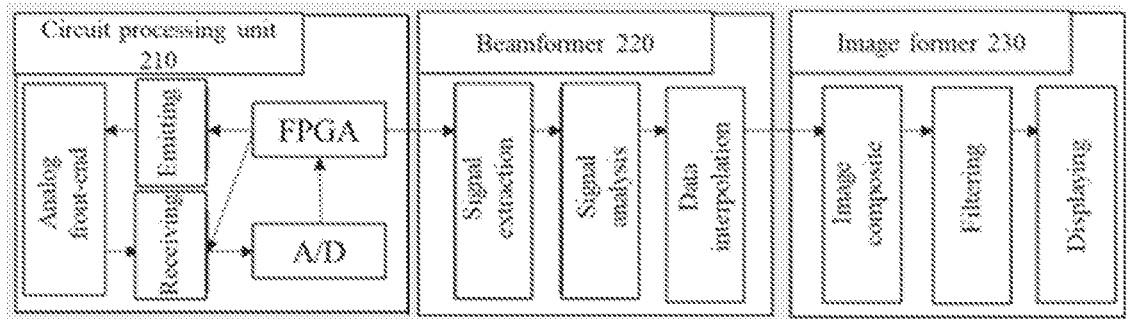
FIG. 2 is a schematic diagram illustrating an exemplary processing device of an ultrasonic imaging system according to some embodiments of the present disclosure.

In some embodiments, the processing device 120 may include a central processing unit (CPU), a digital signal processor (DSP), a system on a chip (SoC), a microcontroller unit (MCU), or the like, or any combination thereof. As shown in FIG. 2, the processing device 120 may include a circuit processing unit 210, a beamformer 220, and an image former 230.

In some embodiments, the circuit processing unit 210 may include an analog front-end circuit, an emitting and receiving circuit, an A/D analog-to-digital conversion circuit, and an FPGA controller.

The analog front-end circuit may directly apply electric signal pulse(s) to the ultrasonic probe and control the ultrasonic probe to emit ultrasonic waves according to an emission aperture determined dynamically in each emission. In some embodiments, the analog front-end circuit may also include a variable gain amplifier for amplifying or suppressing an analog ultrasonic echo signal received by the ultrasonic probe. More descriptions of the variable gain amplifier may be found in the descriptions of operation 730.

The FPGA controller may obtain control instructions (for example, emitting instructions, gaining instructions, receiving instructions and/or idle instructions), and, based on the control instructions, instruct other units or modules to emit ultrasonic wave(s), receive ultrasonic echo signal(s) and obtain ultrasonic image(s) based on ultrasonic echo signal(s). The FPGA controller may also control the emitting and receiving circuits, compress the data after A/D analog-to-digital conversion, and then transmit the compressed data to the beamformer 220.

The beamformer 220 may realize signal extraction, signal analysis and/or data interpolation for each of ultrasonic echo signals. More descriptions of the beamformer 220 may be found in the descriptions of operation 740.

The image former 230 may receive information from the beamformer 220. In some embodiments, the image former 230 may perform spatial filtering, image rendering, image compression, scan conversion and/or other processing on the information from the beamformer. More descriptions of the image former 230 may be found in the descriptions of operation 740.

In some embodiments, the processing device 120 may include a computer, a user console, a single server or a server group. The server group may be centralized or distributed. In some embodiments, the processing device 120 may be local or remote. For example, the processing device 120 may access information and/or data stored in the ultrasonic probe 110, the terminal device 130 and/or the storage device 150 via the network 140. As another example, the processing device 120 may directly connect the ultrasonic probe 110, the terminal device 130 and/or the storage device 150 to access the stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 or a portion of the processing device 120 may be integrated into the ultrasonic probe 110.

The terminal device 130 may receive instruction(s) (e.g., an instruction of ultrasonic examination mode) from a user and may also display ultrasonic image(s) to the user. The terminal device 130 may include a mobile device 131, a tablet computer 132, a notebook computer 133, or the like, or any combination thereof. In some embodiments, the terminal device 130 may be a portion of the processing device 120.

The network 140 may include any suitable network that facilitates the exchange of information and/or data of the ultrasonic imaging system 100. In some embodiments, one or more components of the ultrasonic imaging system 100 (e.g., the ultrasonic probe 110, the processing device 120, the storage device 150, the terminal device 130) may communicate information and/or data with one or more other components of the ultrasonic imaging system 100 through network 140. For example, the processing device 120 may receive user instruction(s) from the terminal device via a network. As another example, the ultrasonic probe 110 may obtain emission parameter(s) from the processing device 120 via the network 140. The network 140 may be and/or may include a public network (e.g., the Internet), a private network (e.g., a local area network (LAN), a wide area network (WAN)), a wired network (e.g., an Ethernet), a wireless network (e.g., an 802.11 network, a Wi-Fi network), a cellular network (e.g., a long term evolution (LTE) network), a frame relay network, a virtual private network ("VPN"), a satellite network, a telephone network, a router, a hub, a switch, a server computer, or the like, and/or any combination thereof. Merely by way of example, the network 140 may include a cable network, a wireline network, an optical fiber network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 140 may include one or more network access points. For example, the network 140 may include wired or wireless network access points such as base stations and/or internet exchange points, through which one or more components of the ultrasonic imaging system 100 may be connected to the network 140 to exchange data and/or information.

The storage device 150 may store data, instruction(s), and/or any other information. In some embodiments, the storage device 150 may store data obtained from the ultrasonic probe 110, the terminal device 130, and/or the processing device 120. In some embodiments, the storage device 150 may store data and/or instruction(s), and the processing device 120 may execute or use the data and/or instruction(s) to execute the exemplary method(s)/system(s) described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDRSDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 140 to communicate with one or more other components of the ultrasonic imaging system 100 (e.g., the ultrasonic probe 110, the processing device 120, the storage device 150, the terminal device 130). One or more components of the ultrasonic imaging system 100 may access data and/or instruction(s) stored in the storage device 150 through the network 140. In some embodiments, the storage device 150 may be directly connected to or communicate with one or more other components of the ultrasonic imaging system 100 (e.g., the ultrasonic probe 110, the processing device 120, the storage device 150, the terminal device 130). In some embodiments, the storage device 150 may be a portion of the processing device 120.

Figure 3:
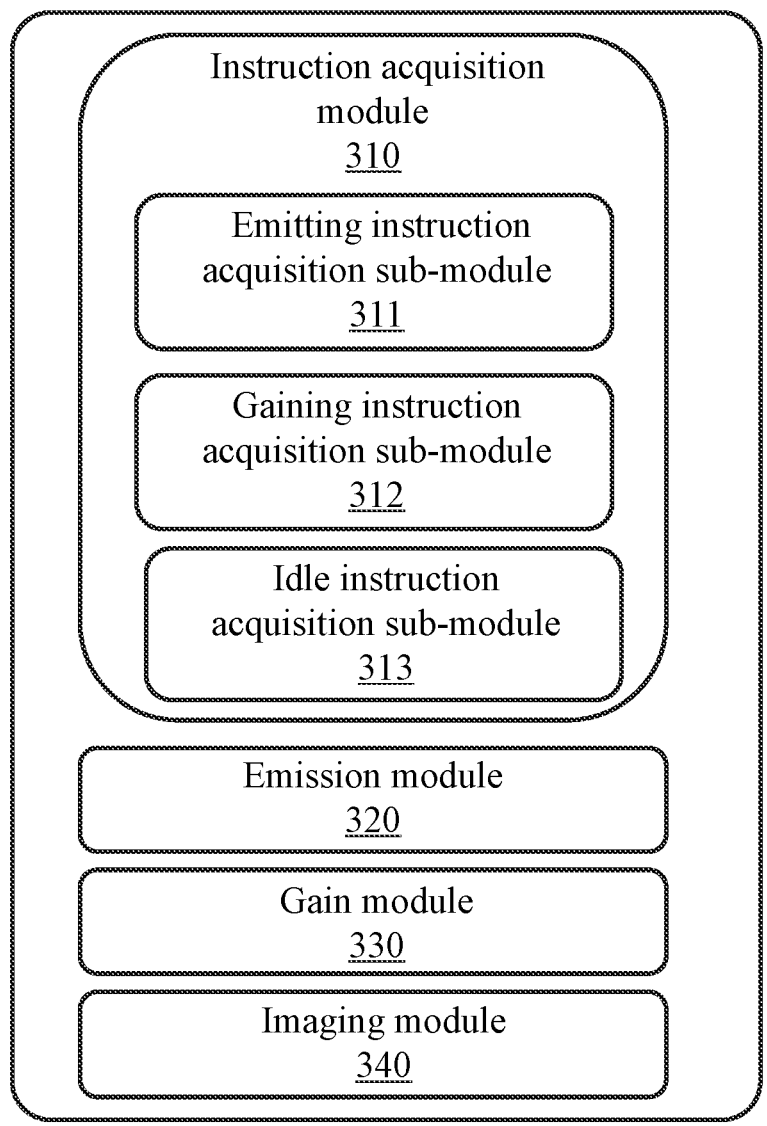
FIG. 3 is a block diagram illustrating an exemplary ultrasonic imaging system according to some embodiments of the present disclosure.

FIG. 3 is a block diagram illustrating an exemplary ultrasonic imaging system according to some embodiments of the present disclosure.

In some embodiments, the processing device 120 may include an instruction acquisition module 310, an emission module 320, a gain module 330, and an imaging module 340.

The instruction acquisition module 310 may be configured to obtain one or more emitting instructions for emitting a plurality of ultrasonic waves, one or more gaining instructions relating to the plurality of ultrasonic waves, one or more receiving instructions relating to the plurality of ultrasonic waves, and/or one or more idle instructions relating to the plurality of ultrasonic waves, and/or store the one or more emitting instructions, the one or more receiving instructions, the one or more gaining instructions and/or the one or more idle instructions in a ring buffer.

In some embodiments, the instruction acquisition module 310 may include an emitting instruction acquisition sub-module 311. The emitting instruction acquisition sub-module 311 may be configured to obtain a focus position corresponding to each emission of the plurality of ultrasonic waves, an effective array element corresponding to each emission and/or a pulse of the plurality of ultrasonic waves.

Figure 4:
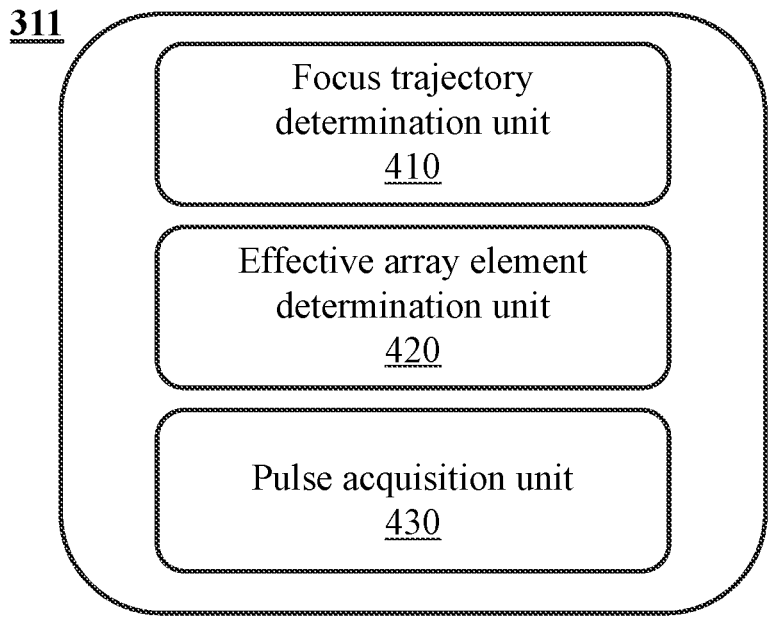
FIG. 4 is a block diagram illustrating an exemplary emitting instruction acquisition sub-module according to some embodiments of the present disclosure.

As shown in FIG. 4, the emitting instruction acquisition sub-module 311 may include a focus trajectory determination unit 410, an effective array element determination unit 420 and a pulse acquisition unit 430.

Figure 5:
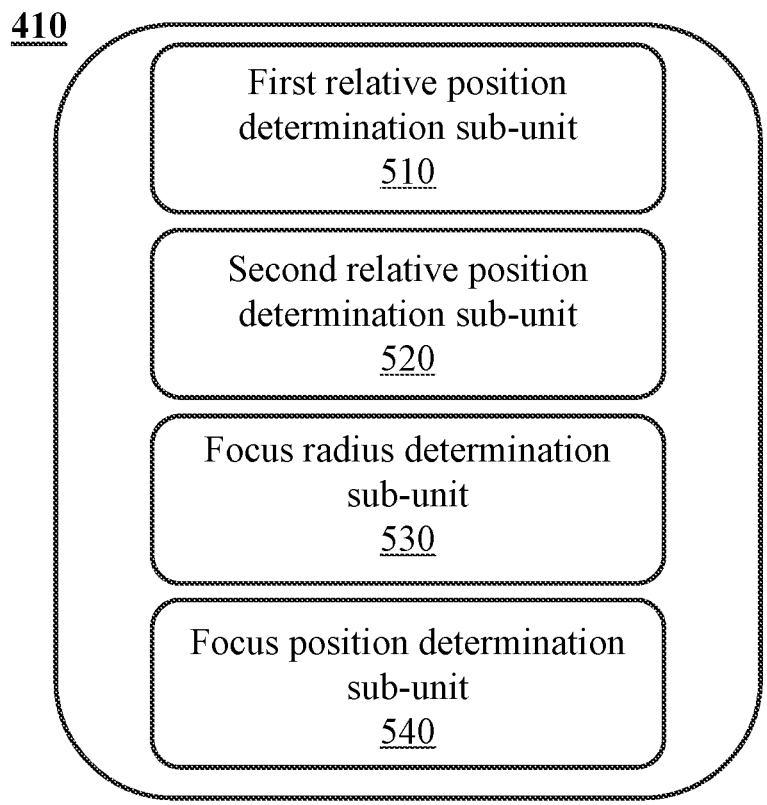
FIG. 5 is a block diagram illustrating an exemplary focus trajectory determination unit according to some embodiments of the present disclosure.

In some embodiments, the one or more emitting instructions for emitting a plurality of ultrasonic waves may include the focus position corresponding to each emission. The focus trajectory determination unit 410 may be configured to determine the focus position corresponding to each emission. As shown in FIG. 5, the focus trajectory determination unit 410 may include a first relative position determination sub-unit 510, a second relative position determination sub-unit 520, a focus radius determination sub-unit 530, and a focus position determination sub-unit 540.

The first relative position determination sub-unit 510 may be configured to determine a first relative position corresponding to each emission based on the emission times and/or an emission order of the plurality of ultrasonic waves, to obtain a plurality of first relative positions corresponding to the plurality of emissions. More descriptions of the first relative position determination sub-unit may be found in the descriptions of operation 910.

The second relative position determination sub-unit 520 may be configured to map the plurality of first relative positions distributed at equal intervals to a plurality of second relative positions distributed at unequal intervals corresponding to the plurality of emissions. In some embodiments, the second relative position determination sub-unit may be configured to map the plurality of first relative positions distributed at equal intervals to the plurality of second relative positions distributed at unequal intervals corresponding to the plurality of emissions through a nonlinear curve. More descriptions of the second relative position determination sub-unit may be found in the descriptions of operation 920.

The focus radius determination sub-unit 530 may be configured to determine an emission distance and a focus radius corresponding to each emission based on an emission parameter and the second relative position corresponding to each emission. In some embodiments, the emission parameter may include a count of transducer channels, an array element width and a curvature of the transducer. In some embodiments, the focus radius determination sub-unit 530 may be configured to perform one or more of the following operations: determining the emission distance corresponding to each emission based on the count of channels of the transducer, the array element width and the second relative position corresponding to the each emission; determining the focus radius corresponding to the each emission based on the emission distance corresponding to the each emission, the second relative position corresponding to the each emission and the curvature of the transducer. The focus radius determination sub-unit may determine a focus curvature corresponding to each emission based on the emission distance corresponding to the each emission, the second relative position corresponding to the each emission and the curvature of the transducer. The focus radius determination sub-unit may determine whether an absolute value of the focus curvature corresponding to the each emission is less than a curvature threshold. In response to a determination that the absolute value of the focus curvature corresponding to each emission is less than the curvature threshold, the focus radius determination sub-unit may designate a reciprocal of the curvature threshold as the focus radius, and determine a direction of the focus radius based on the focus curvature. In response to a determination that the absolute value of the focus curvature corresponding to each emission is not less than the curvature threshold, the focus radius determination sub-unit may designate a reciprocal of the focus curvature as the focus radius. More descriptions of the focus radius determination sub-unit may be found in the descriptions of operation 930.

The focus position determination sub-unit 540 may determine the focus position corresponding to each emission based on the emission distance and the focus radius corresponding to the each emission. In some embodiments, the focus position determination sub-unit 540 may perform one or more of the following operations: obtaining a radian corresponding to the emission distance corresponding to each emission based on the emission distance corresponding to the each emission and the curvature of the transducer; obtaining projection distances of the emission distance corresponding to the each emission on a transversal axis and a longitudinal axis respectively based on the radian corresponding to the emission distance corresponding to the each emission; obtaining an abscissa of the focus corresponding to the each emission based on the projection distance of the emission distance corresponding to the each emission on the transversal axis, the focus radius, and the curvature of the transducer; obtaining an ordinate of the focus corresponding to the each emission based on the projection distance of the emission distance corresponding to the each emission on the longitudinal axis, the focus radius, and the curvature of the transducer. More descriptions of the focus position determination sub-unit may be found in the descriptions of operation 940.

Figure 6:
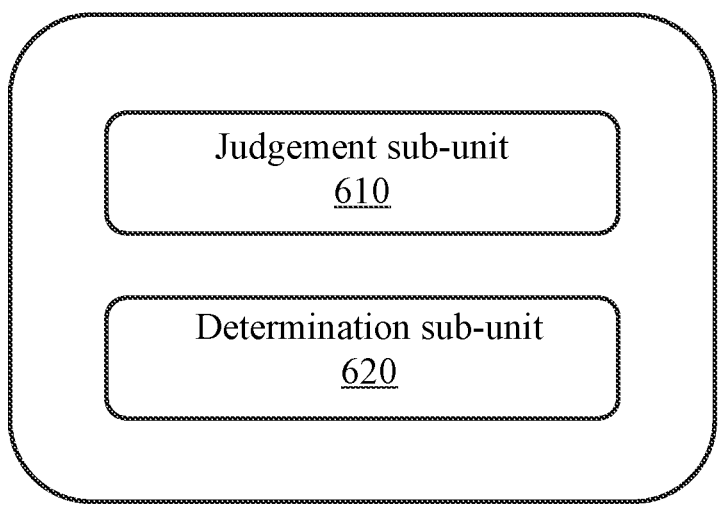
FIG. 6 is a block diagram illustrating an exemplary effective array element determination unit according to some embodiments of the present disclosure.

In some embodiments, the one or more emitting instructions for emitting a plurality of ultrasonic waves may include an effective array element (also referred to as an effective aperture) corresponding to each emission. The effective array element determination unit 420 may be configured to determine the effective array element corresponding to each emission. As shown in FIG. 6, the effective array element determination unit 420 may include a judgement sub-unit 610 and a determination sub-unit 620.

The judgement sub-unit 610 may judge whether there is an invalid array element in an emission. For example, the judgement sub-unit 610 may judge whether there is an invalid array element in each emission based on a radius of a transducer, an array element width and/or the focus position corresponding to the each emission. In some embodiments, the judgement sub-unit 610 may perform one or more of the following operations: determining a maximum value of an array element pointing angle corresponding to the emission of the ultrasonic wave based on the array element width; determining a maximum pointing circle corresponding to the maximum value of the array element pointing angle based on the radius of the transducer and the maximum value of the array element pointing angle; determining whether the focus position is within the maximum pointing circle. In response to a determination that the focus position is within the maximum pointing circle, the judgement sub-unit 610 may determine that there is no invalid array element in the emission of the ultrasonic wave. In response to a determination that the focus position is not within the maximum pointing circle, the judgement sub-unit 610 may determine that there is at least one invalid array element in the emission of the ultrasonic wave. More descriptions of the judgement sub-unit 610 may be found in the descriptions of operation 1210.

The determination sub-unit 620 may determine an effective array element corresponding to an emission. For example, the determination sub-unit 620 may determine the effective array element corresponding to the emission based on the radius of the transducer, the width of the array element and/or the focus position in response to an existence of invalid array element(s) in the emission, or determine all array elements of the transducer as effective array elements in response to an absence of invalid array element(s) in the emission. In some embodiments, the determination sub-unit 620 may perform one or more of the following operations: determining a first deflection angle based on the radius of the transducer, and/or the focus position, wherein the first deflection angle refers to an angle between a connecting line of a center of the transducer and the focus position and a central axis of the transducer; determining a second deflection angle based on the maximum pointing circle, the radius of the transducer, and/or the focus position, wherein the second deflection angle refers to an angle between the connecting line of the center of the transducer and the focus position and a tangent of the maximum pointing circle passing through the focus position; determining a first slope of a first connecting line between the focus position and an initial left boundary effective array element based on a difference between the first deflection angle and the second deflection angle; determining a second slope of a second connecting line between the focus position and an initial right boundary effective array element based on a sum of the first deflection angle and the second deflection angle; obtaining a left boundary effective array element and a right boundary effective array element based on the first slope, the second slope, the radius of the transducer, and/or a boundary of all array elements to determine the effective array element corresponding to the emission of the ultrasonic wave. In some embodiments, the determination sub-unit 620 may determine a position of the initial left boundary effective array element and/or a position of the initial right boundary effective array element based on the first slope, the second slope and/or the radius of the transducer. The position of the initial left boundary effective array element and the position of the initial right boundary effective array element may meet an array element directivity restriction condition. In response to a determination that the position of the initial left boundary effective array element and/or the position of the initial right boundary effective array element are within the boundary of all array elements, the determination sub-unit 620 may take the initial left boundary effective array element and/or the initial right boundary effective array element as the left boundary effective array element and/or the right boundary effective array element, respectively. In response to a determination that the position of the initial left boundary effective array element and/or the position of the initial right boundary effective array element is not within the boundary of all array elements, the determination sub-unit 620 may designate array elements at the boundary of all array elements as the left boundary effective array element and/or the right boundary effective array element. More descriptions of the determination sub-unit 620 may be found in the descriptions of operation 1220, 1230 and/or 1240.

In some embodiments, the one or more emitting instructions for emitting the plurality of ultrasonic waves may include pulses of the plurality of ultrasonic waves. The pulse acquisition unit 430 may be configured to obtain pulses of the plurality of ultrasonic waves. In some embodiments, the pulse acquisition unit 430 may perform one or more of the following operations: dividing at least one portion of the pulses of the plurality of ultrasonic waves into a transmission group, wherein the transmission group includes N pulses, wherein N≥1, and each pulse of the N pulses corresponds to at least one of a positive value, a negative value or zero; compressing the transmission group into compressed data and transmitting the compressed data; decoding the compressed data to obtain the at least one portion of the pulses. In some embodiments, the transmission group may also include at least one portion of the gaining instructions. More descriptions of the pulse acquisition unit 430 may be found in FIG. 14 and its related descriptions.

In some embodiments, the instruction acquisition module 310 may include a gaining instruction acquisition sub-module 312. The gaining instruction acquisition sub-module 312 may perform one or more of the following operations: determining at least one medium propagation time corresponding to at least one depth value of a target object based on an effective aperture corresponding to each emission and/or the at least one depth value, wherein the at least one medium propagation time includes at least one emission time and/or at least one ultrasonic echo time; determining at least one gain value corresponding to the at least one depth value based on an attenuation index of ultrasonic propagation, a noise value and the at least one medium propagation time. More descriptions of the gaining instruction acquisition sub-module 312 may be found in FIG. 16 and its related descriptions.

In some embodiments, the instruction acquisition module 310 may include an idle instruction acquisition sub-module 313. In some embodiments, an idle instruction may be used to control or indicate that the ultrasonic probe is in idle time, and the idle time may include intra frame time and/or inter frame time. The idle instruction acquisition sub-module 313 may obtain at least one set of historical ultrasonic imaging data based on a trigger condition; obtain a historical imaging time based on the at least one set of historical ultrasonic imaging data; determine whether the inter frame time and the historical imaging time meet a predetermined condition, wherein the inter frame time is an interval time between emissions of ultrasonic waves corresponding to two adjacent image frames; in response to a determination that the inter frame time and the historical imaging time meet the predetermined condition, update the inter frame time to the historical imaging time; and in response to a determination that the inter frame time and the historical imaging time do not meet the predetermined condition, refrain from updating the inter frame time. In some embodiments, the at least one set of historical ultrasonic imaging data may include at least one of ultrasonic propagation time, imaging time, and image processing time.

More descriptions of the instruction acquisition module 310 may be found in the descriptions of operation 710.

The emission module 320 may be configured to obtain the one or more emitting instructions for emitting the plurality of ultrasonic waves from a ring buffer and emit the plurality of ultrasonic waves based on the one or more emitting instructions. In some embodiments, the emission module 320 may emit the plurality of ultrasonic waves to the target object based on the effective aperture corresponding to each emission. More descriptions of the emission module 320 may be found in the descriptions of 720.

The gain module 330 may be used to obtain a gaining instruction and a receiving instruction corresponding to each emission of the plurality of ultrasonic waves from the ring buffer, and obtain at least one enhanced echo signal based on the one or more gaining instructions and the one or more receiving instructions. In some embodiments, the gain module 330 may obtain at least one initial echo signal corresponding to each emission based on the one or more receiving instructions. In some embodiments, the gain module 330 may perform an analog gain operation on at least one initial echo signal corresponding to the each emission based on the one or more gaining instructions to obtain at least one enhanced echo signal. More descriptions of the gain module 330 may be found in the descriptions of 730.

The imaging module 340 may be used to obtain the one or more idle instructions relating to the plurality of ultrasonic waves from the ring buffer, and process at least one enhanced echo signal based on the one or more idle instructions to obtain a target ultrasonic image. The imaging module 340 may process the at least one enhanced echo signal within the intra frame time to obtain the ultrasonic image information corresponding to each emission. In some embodiments, processing the at least one enhanced echo signal may include at least one of signal extraction, signal analysis, and data interpolation. The imaging module 340 may compose the ultrasonic image information corresponding to the plurality ultrasonic waves within the inter frame time to obtain an initial ultrasonic image corresponding to the plurality of ultrasonic waves. The imaging module 340 may perform a digital gain operation on the initial ultrasonic image based on at least one gain value. The imaging module 340 may process the initial ultrasonic image after gaining to obtain the target ultrasonic image. In some embodiments, the processing the initial ultrasonic image after gaining includes at least one of spatial filtering, image rendering, image compression or scanning conversion. More descriptions of the imaging module 340 may be found in the descriptions of operation 740.

FIG. 7 is a flowchart illustrating an exemplary ultrasonic imaging process according to some embodiments of the present disclosure.

Ultrasonic images refer to internal tissue images obtained by receiving and processing scanning data that is generated by scanning a target object using ultrasonic waves for medical treatment or medical research.

In some embodiments, the target object may be a human body, organs, a body, an object, an injury site, a tumor, or the like. For example, the target object may be one or more diseased tissues of a patient's heart.

The scanning data may be or correspond to one or more ultrasonic echo signals received from the target object or a portion of the target object by emitting ultrasonic waves to the target object or a portion of the target object through the ultrasonic probe.

In some embodiments, image formats of the ultrasonic images may include joint photographic experts group (JPEG), tagged image file format (TIFF), graphics interchange format (GIF), Kodak flash pix (FPX), digital imaging and communication in medicine (DICOM), or the like.

The transducer is an integral part of the ultrasonic probe. The transducer may convert electrical signals into ultrasonic signals through an array element (also known as an aperture) to emit the ultrasonic signals to the target object or a portion of the target object, or convert the ultrasonic echo signals of the target object or a portion of the target object into electrical signals (i.e., the scanning data) to generate ultrasonic image(s). The array element may include piezoelectric material(s), such as barium titanate, lead titanate, lead zirconate titanate, or the like. In some embodiments, the transducer may include array elements with a plurality of frequencies, and channels (i.e., control circuits) of the transducer corresponding to the array elements. The transducer may excite the array elements at different positions by the electrical signal(s) through the channels of the transducer to produce ultrasonic waves with different frequencies. Specifically, the transducer may transmit a pulse signal to a corresponding channel of the transducer, and each channel of the transducer may excite the corresponding array element based on a corresponding pulse signal, to emit ultrasonic waves with different or the same frequency at different or the same time.

Generally, when the ultrasonic probe is in a working state, the array element of the transducer may have three states: emitting state, receiving state, and idle state. The three states of the array element may be converted through the one or more emitting instructions, the one or more receiving instructions and the one or more idle instructions transmitted by the FPGA controller. At the same time, the FPGA controller may also transmit a control instruction (i.e., a gaining instruction) of the variable gain device to process the scanning data received by the array element. It should be understood that in a process of obtaining an ultrasonic image, the ultrasonic imaging system may need to continuously switch between the emitting state, the receiving state, and the idle state based on the one or more emitting instructions, the one or more gaining instructions, the one or more receiving instructions, and the one or more idle instructions, resulting in the need for the storage device to continuously store or take out the one or more emitting instructions, the one or more gaining instructions, the one or more receiving instructions, and the one or more idle instructions. Ordinary storage devices need to reallocate all memory every time they store or take out the control instructions. Therefore, in order to avoid the increase of system overhead and memory fragments caused by frequent memory allocation and release, which eventually leads to the slow operation of the system, ring buffer may be configured to store and take out the control instructions in the process of the ultrasonic imaging, and obtain the target ultrasonic image based on the control instructions. As shown in FIG. 7, the ultrasonic imaging process 700 may include one or more of the following operations.

In 710, one or more emitting instructions for emitting a plurality of ultrasonic waves, one or more gaining instructions relating to the plurality of ultrasonic waves, one or more receiving instructions relating to the plurality of ultrasonic waves, and one or more idle instructions relating to the plurality of ultrasonic waves may be obtained, and the one or more emitting instructions, the one or more receiving instructions, the one or more gaining instructions, and the one or more idle instructions may be stored in a ring buffer.

Specifically, the operation 710 may be implemented by the instruction acquisition module 310.

An emitting instruction may be an instruction that instructs the ultrasonic probe to emit one or more ultrasonic waves according to one or more emission parameters. In some embodiments, the instruction acquisition module 310 may obtain the one or more emitting instructions through the emitting instruction acquisition sub-module 311.

An emission parameter may be a parameter configured to control emission of one or more of the plurality of ultrasonic waves. In some embodiments, the emission parameter(s) may include a count of channels of a transducer, an array element width and a curvature of the transducer (or a radius of the transducer), and/or a boundary of the array element. More descriptions of the count of channels of the transducer, the array element width and the curvature of the transducer (or the radius of the transducer), and the boundary of the array element may be found in FIGS. 9 and 12, and their related descriptions.

In some embodiments, the one or more emitting instructions for emitting a plurality of ultrasonic waves may include at least one of a focus position corresponding to each emission, the effective array element corresponding to the each emission, and/or the pulses of the plurality of ultrasonic waves.

A focus may be an intersection of extension lines of an ultrasonic beam on the target object or a portion of the target object.

Figure 11A:
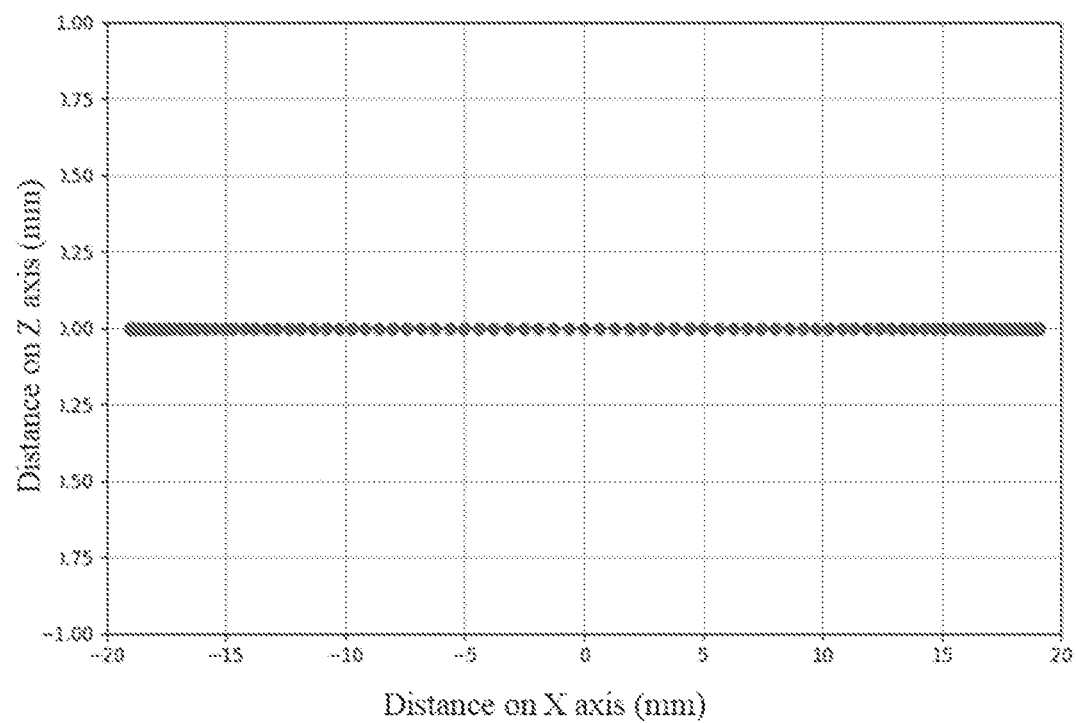
FIG. 11a is a schematic diagram illustrating an exemplary focus trajectory of ultrasonic emission of a linear array ultrasonic probe according to some embodiments of the present disclosure.

In some embodiments, the emitting instruction acquisition sub-module 311 may automatically determine the focus trajectory fixedly matched with the ultrasonic probe based on the ultrasonic probe selected by a user. For example, when the user selects a linear array ultrasonic probe, the emitting instruction acquisition sub-module 311 may determine the focus trajectory as shown in FIG. 11*a*.

In some embodiments, the emitting instruction acquisition sub-module 311 may also determine the focus trajectory based on an ultrasonic examination mode input by the user. For example, if the user selects "belly examination mode", the emitting instruction acquisition sub-module 311 may determine the corresponding convex array ultrasonic probe and the focus trajectory as shown in FIG. 12*a*.

In some embodiments, the emitting instruction acquisition sub-module 311 may also design a focus trajectory to compensate for the energy loss on one or both sides of the ultrasonic probe based on the emission parameter(s) through the focus trajectory determination unit 410 to obtain the focus position corresponding to each emission. More descriptions for determining the focus position corresponding to each emission may be found in FIG. 9 and its related description.

The transducer of the ultrasonic probe may excite the array elements at different positions with electrical signals through the channels of the transducer, to produce ultrasonic waves with different frequencies. The effective array element (also referred to as the effective aperture) may be the array element excited by the electrical signal corresponding to each emission. In some embodiments, the ultrasonic probe may excite the corresponding effective array element to emit ultrasonic waves based on the focus corresponding to each emission.

In some embodiments, the emitting instruction acquisition sub-module 311 may divide all array elements into one or more groups based on setting parameter(s) provided by the user, to determine the effective array element(s) in each group of the array element corresponding to each emission. For example, the ultrasonic probe may include 100 array elements. Based on a group number "5" input by the user, the effective array elements corresponding to the first, second, . . . , fifth emission may be determined as: the 1st~20th array element, the 21st~31st array element, . . . , the 91st~100th array element.

In some embodiments, the emitting instruction acquisition sub-module 311 may also determine the effective array element(s) corresponding to each emission based on the geometric relationship between the array element directivity and the focus position through the effective array element determination unit 420. Mores descriptions of determining the effective array element(s) corresponding to each emission based on the geometric relationship between the array element directivity and the focus position may be found in FIG. 12 and its related descriptions.

An amplitude and/or a direction of an electric signal exciting the array elements at different positions may determine a frequency and/or an amplitude of a corresponding ultrasonic wave. Each group of electrical signals may include a plurality of pulses. In some embodiments, the plurality of pulses corresponding to the plurality of ultrasonic waves may be determined by the processing device 120 based on a user instruction obtained from the terminal device 130. For example, if the user inputs the ultrasonic examination mode (e.g., "belly examination mode") through the terminal device 130, the processing device 120 may determine the plurality of pulses corresponding to the plurality of ultrasonic waves based on the "belly examination mode." Further, the emitting instruction acquisition sub-module 311 may obtain one or more corresponding pulses from the processing device 120.

In some alternative embodiments, the one or more emitting instructions may include no pulse, but include an instruction for instructing the processing device 120 to transmit corresponding pulse(s) to the ultrasonic probe 110, thus the ultrasonic probe 110 may generate ultrasonic waves based on the pulse(s).

It can be understood that the efficiency of transmitting pulses from the storage device 150 (e.g., the ring buffer) or the processing device 120 to the ultrasonic probe 110 may affect the efficiency of ultrasonic imaging. Therefore, an efficient pulse transmission mode is needed. More descriptions of transmitting pulse(s) may be found in FIG. 14 and its related descriptions.

The gaining instruction may be configured to obtain at least one portion of gain parameter(s) of ultrasonic echo signal(s) emitted by the ultrasonic wave or the gaining of the ultrasonic echo signal(s). The gain parameter(s) may include an amplification factor (or gain) that enhances a corresponding ultrasonic echo signal. In some embodiments, the gain parameter(s) may include at least one of a gain compensation coefficient for an analog gain operation and a gain value for a digital gain operation.

The gain compensation coefficient may be a primary compensation gain parameter, which may be used to roughly adjust and amplify the ultrasonic echo signal. More descriptions of the gain compensation coefficient may be found in the descriptions of operation 730.

The gain value may be a secondary compensation gain parameter, which may be used to adjust and amplify the ultrasonic echo signal after primary compensation more finely. More descriptions for obtaining the gain value of the ultrasonic echo signal may be found in FIG. 16 and its related description.

In some alternative embodiments, only a portion of the gain parameter(s) may be stored in the one or more gaining instructions, while another portion of the gain parameter(s) may be calculated in real time based on the one or more gaining instructions. For example, the one or more gaining instructions may be used to store only the gain value, or store an instruction instructing the variable gain amplifier to calculate the gain compensation coefficient without storing the gain compensation coefficient. As another example, the one or more gaining instructions may be used to store only the gain compensation coefficient, or store an instruction instructing the variable gain amplifier to calculate the gain value without storing the gain value.

The one or more receiving instructions may be used to instruct the ultrasonic probe to receive an ultrasonic signal reflected from the target object or a portion of the target object. In some embodiments, the one or more receiving instructions may include an ultrasonic echo time for each ultrasonic echo signal and/or a reception array element for receiving each ultrasonic echo signal. More descriptions for determining the ultrasonic echo time and/or the reception array element may be found in the descriptions of operation 1610.

The idle instruction may be used to instruct the ultrasonic probe to suspend emitting ultrasonic waves, and/or instruct the processing device to obtain an ultrasonic image based on received signal(s). In some embodiments, the instruction acquisition module 310 may obtain the one or more idle instructions through the idle instruction acquisition sub-module 313. In some embodiments, the one or more idle instructions may control or indicate that the ultrasonic probe is in idle time, which may include the intra frame time and/or the inter frame time.

The intra frame time may be an interval time for emitting ultrasonic waves corresponding to each image frame. For example, a plurality of ultrasonic waves may need to be emitted to form an image frame, the time between two adjacent emissions may be regarded as the intra frame time. In the intra frame time, the ultrasonic probe may switch between the emitting state and the receiving state, and the processing device may process the received ultrasonic echo signal(s) and obtain ultrasonic image information. In some embodiments, the idle instruction acquisition sub-module 313 may obtain the intra frame time based on the ultrasonic examination mode input by the user.

The inter frame time may be an interval time between emissions of ultrasonic waves corresponding to two adjacent image frames. For example, the interval time between the last emission for forming one image frame and the first emission for forming the next frame image may be regarded as the inter frame time. The processing device may obtain or generate an ultrasonic image based on the ultrasonic image information in the inter frame time.

In some embodiments, the idle instruction acquisition sub-module 313 may be used to determine the inter frame time based on user settings.

In some embodiments, the idle instruction acquisition sub-module 313 may also determine the inter frame time based on the historical ultrasonic imaging data. More descriptions for determining the inter frame time based on the historical ultrasonic imaging data may be found in FIG. 18 and its related descriptions.

In some embodiments, the instruction acquisition module 310 may store the one or more emitting instructions, the one or more receiving instructions, the one or more gaining instructions, and/or the one or more idle instructions in any position in the ring buffer in any order, and return a storage position to the processing device 120, thus the processing device 120 may call any one of the one or more emitting instructions, the one or more receiving instructions, the one or more gaining instructions, and the one or more idle instructions from the ring buffer through the network 140 (e.g., an interface) based on the storage position.

Figure 8:
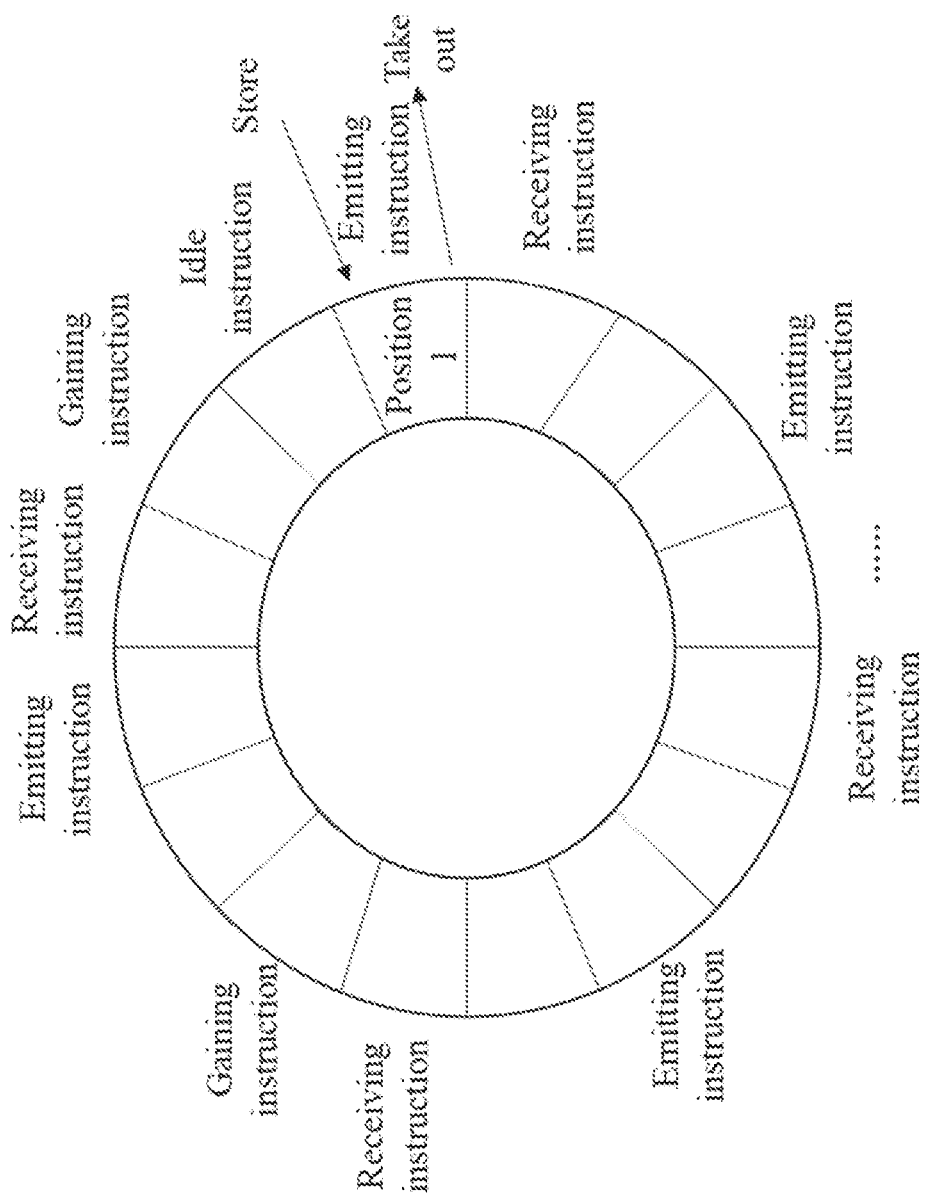
FIG. 8 is a schematic diagram illustrating an exemplary ring buffer according to some embodiments of the present disclosure.

As shown in FIG. 8, the instruction acquisition module 310 may be used to store the one or more emitting instructions in "position 1" in the ring buffer and return the storage position "position 1" to the processing device 120, thus the processing device 120 may call an emitting instruction of the one or more emitting instructions from the ring buffer (e.g., through the interface) based on the storage position "position 1".

In 720, the one or more emitting instructions may be obtained from the ring buffer, and the plurality of ultrasonic waves may be emitted based on the one or more emitting instructions.

Specifically, the operation 720 may be implemented by the emission module 320.

In some embodiments, the emission module 320 may obtain the one or more emitting instructions from the ring buffer through the network 140.

Further, the emission module 320 may determine an amplitude and/or a direction of the electrical signal that excites the effective array element(s) corresponding to each emission based on the pulses of the plurality ultrasonic waves according to the one or more emission instructions, and use the electrical signal to excite the effective array element(s) corresponding to each emission according to the one or more emission instructions, thus the effective array element(s) may emit the plurality of ultrasonic waves.

In 730, a gaining instruction of the one or more gaining instructions and/or a receiving instruction of the one or more receiving instructions corresponding to each emission of the plurality of ultrasonic waves may be obtained from the ring buffer, and at least one enhanced echo signal may be obtained based on the one or more gaining instructions and/or the one or more receiving instructions.

Specifically, the operation 730 may be implemented by the gain module 330.

In some embodiments, the gain module 330 may obtain the one or more gaining instructions and/or the one or more receiving instructions corresponding to each emission of the plurality of ultrasonic waves from the ring buffer through the network 140.

In some embodiments, the gain module 330 may obtain at least one initial echo signal corresponding to each emission from the reception array element specified in the one or more receiving instructions based on the one or more receiving instructions. Specifically, the gain module 330 may use the reception array element to receive the ultrasonic echo signal(s) emitted from the target object or a portion of the target object, and convert mechanical vibration generated by the reception array element into an electrical signal, that is, the initial echo signal.

Further, the gain module 330 may perform an analog gain operation on the at least one initial echo signal corresponding to each emission based on the one or more gaining instructions to obtain at least one enhanced echo signal. Specifically, the gain module 330 may obtain a gain compensation coefficient through a variable gain amplifier. Specifically, the gaining instruction acquisition sub-module 312 may determine the gain compensation coefficient corresponding to each ultrasonic echo signal based on the emission time corresponding to each emission and/or the ultrasonic echo time of each ultrasonic echo signal. More descriptions of the emission time and ultrasonic echo time may be found in the descriptions of operation 1610.

In some embodiments, the instruction acquisition module 310 may obtain an analog gain compensation coefficient corresponding to the ultrasonic echo signal by comparing a time difference of the emission time corresponding to each emission and/or the ultrasonic echo time of a corresponding one of the plurality of ultrasonic echo signals with a reference time difference threshold or a threshold range. For example, an ultrasonic wave may correspond to a plurality of ultrasonic echo signals. The time difference between the emission time corresponding to the ultrasonic wave and the ultrasonic echo time corresponding to an i-th ultrasonic echo signal in the plurality of ultrasonic echo signals is ti. If ti is less than the reference time difference threshold T, the analog gain compensation coefficient corresponding to the ultrasonic echo signal may be designated as k1. If ti is greater than the reference time difference threshold T, the analog gain compensation coefficient corresponding to the ultrasonic echo signal may be designated as k2, wherein k1 and k2 may be set based on experience values.

In some embodiments, the instruction acquisition module 310 may also determine the analog gain compensation coefficient corresponding to the ultrasonic echo signal based on the time difference corresponding to the above-mentioned ultrasonic echo signal and the time difference between a previous ultrasonic echo signal and a posterior ultrasonic echo signal.

Further, the variable gain amplifier may multiply each initial echo signal by each corresponding gain compensation coefficient included in the one or more gaining instructions to obtain each corresponding enhanced echo signal.

In some embodiments, the gain compensation coefficient may also be stored in the one or more gaining instructions of the ring buffer based on the gaining instruction acquisition sub-module in advance. The variable gain amplifier may obtain the gain compensation coefficient based on the one or more gaining instructions to perform the analog gain operation on the ultrasonic echo signal.

In 740, the one or more idle instructions relating to the plurality of ultrasonic waves may be obtained from the ring buffer, and the at least one enhanced echo signal may be processed based on the one or more idle instructions to obtain a target ultrasonic image.

Specifically, the operation 740 may be implemented by the imaging module 340.

In some embodiments, the imaging module 340 may process the at least one enhanced echo signal within the intra frame time to obtain the ultrasonic image information corresponding to each emission.

The ultrasonic image information may be image information of ultrasonic echo signal, which may be expressed in different forms based on different ultrasonic imaging modes. For example, ultrasonic image information corresponding to A-mode ultrasonic imaging may be expressed as a relationship between an amplitude of at least one enhanced echo signal corresponding to each emission and the ultrasonic echo time. As another example, ultrasonic image information corresponding to B-mode ultrasonic imaging may be expressed as a relationship between a position depth reached by each ultrasonic wave in the target object or a portion of the target object and an intensity of the enhanced echo signal reflected from the position depth.

Specifically, the plurality of ultrasonic waves may be emitted within the intra frame time corresponding to each image frame. At the interval between the emission of two adjacent ultrasonic waves, the imaging module 340 may process at least one enhanced echo signal corresponding to a previous ultrasonic wave in the two adjacent ultrasonic waves to obtain the corresponding ultrasonic image information. For example, 20 ultrasonic waves have been emitted within the intra frame time corresponding to an image frame. In the interval between the emission of the first ultrasonic wave and the second ultrasonic wave, the imaging module 340 may process at least one enhanced echo signal corresponding to the first ultrasonic wave and obtain the ultrasonic image information corresponding to the first ultrasonic wave.

In some embodiments, the imaging module 340 may convert an analog enhanced echo signal into a digital enhanced echo signal through the A/D analog-to-digital conversion circuit, then transmit a compressed digital enhanced echo signal to the beamformer, and then process at least one enhanced echo signal through the beamformer. In some embodiments, processing at least one enhanced echo signal may include at least one of signal extraction, signal analysis, and/or data interpolation.

The signal extraction may be a process of decompressing a compressed signal. In order to improve the amount of data transmitted in unit time, the A/D analog-to-digital conversion circuit may compress the enhanced echo signal and transmit the enhanced echo signal to the beamformer, which may decompress the enhanced echo signal through signal extraction.

The signal analysis may be a process of improving the quality of enhanced echo signal based on feature(s) of the enhanced echo signal. In some embodiments, the imaging module 340 may analyze the enhanced echo signal through a filter and/or a machine learning model. In some embodiments, the filter may include, but may not be limited to, at least one or a combination of low-pass filtering (smoothing), high pass filtering (sharpening), and band-pass filtering. In some embodiments, the machine learning model may include, but may not be limited to, a convolutional neural network (CNN) model, a deep neural network (DNN) model, a recurrent neural network (RNN) model, or the like.

The data interpolation may be a process of inserting signal(s). In some embodiments, data interpolation may include, but may not be limited to, at least one of adaptive interpolation algorithms, such as nearest neighbor interpolation, quadratic interpolation, cubic interpolation, or the like. For example, the imaging module may obtain an interpolation between two adjacent enhanced echo signals based on the two adjacent enhanced echo signals. For example, emitting the first ultrasonic wave may correspond to three enhanced echo signals, and the imaging module may obtain the interpolation between the first and second enhanced echo signals based on the first and second enhanced echo signals, and obtain the interpolation between the second and third enhanced echo signals based on the second and third enhanced echo signals, thereby performing two interpolations on the three enhanced echo signals.

In some embodiments, the imaging module 340 may compose the ultrasonic image information corresponding to the plurality of ultrasonic waves in the inter frame time to obtain an initial ultrasonic image corresponding to the plurality of ultrasonic waves.

Specifically, the imaging module 340 may compose ultrasonic image information corresponding to each image frame to obtain an initial ultrasonic image frame, and then compose a plurality of initial ultrasonic image frames after the last emission to obtain the initial ultrasonic image corresponding to the plurality of ultrasonic waves.

Continuing with the above example, the imaging module 340 may compose the 20 pieces of ultrasonic image information corresponding to the 20 ultrasonic waves emitted in the i-th inter frame time to obtain the i-th initial ultrasonic image frame within the inter frame time between the i-th inter frame time and the (i+1)-th inter frame time. Then, after the last intra frame time, the imaging module 340 may compose the N initial ultrasonic image frames corresponding to the N intra frame time, i.e., the first initial ultrasonic image frame, . . . , the i-th initial ultrasonic image frame, . . . , and the N-th initial ultrasonic image frame, and obtain the initial ultrasonic image corresponding to N×20 ultrasonic waves.

In some embodiments, the imaging module 340 may determine a corresponding imaging coordinate based on the ultrasonic imaging mode, and then fuse a plurality of pieces of ultrasonic image information into the same imaging coordinate to obtain an initial ultrasonic image.

Further, the imaging module 340 may perform a digital gain operation on the initial ultrasonic image based on at least one gain value. In some embodiments, the imaging module 340 may multiply a signal intensity corresponding to each point in the initial ultrasonic image by a corresponding gain value. For example, point A may indicate that a signal amplitude at a depth h1 of the target object is 20, and the gain value $\Gamma$ (h1) corresponding to the depth h1 of the target object may be multiplied by 20 to obtain the signal intensity after a gain operation is performed on the point.

Further, the imaging module 340 may process the initial ultrasonic image after the gain operation performed by the image former 230 to obtain the target ultrasonic image. In some embodiments, the process for processing the initial ultrasound image after the gain operation may include at least one of spatial filtering, image rendering, image compression and scanning conversion.

The spatial filtering may be configured to enhance the quality of the initial ultrasonic image. In some embodiments, the spatial filtering may include, but may not be limited to, at least one of low-pass filtering (or smoothing), high pass filtering (or sharpening), band-pass filtering, 3×3 adaptive filtering algorithm, and 5×5 adaptive filtering algorithm, or any combination thereof.

The image rendering may be a process of converting a three-dimensional energy transfer into two-dimensional image(s), and the image rendering may convert the digital enhanced echo signal into image information. In some embodiments, a method for image rendering may include, but may not be limited to, at least one of OpenGL, DirectX, or the like, or any combination thereof.

The image compression may reduce the amount of initial ultrasonic image data. In some embodiments, modes of image compression may include, but may not be limited to, at least one of differential pulse code modulation algorithm, hierarchical interpolation algorithm, differential pyramid algorithm, multiple autoregressive algorithm, discrete cosine transform, or the like, or any combination thereof.

The image conversion may refer to converting the initial ultrasonic image into an ultrasonic image in a target coordinate system. For example, the initial ultrasonic image in a polar coordinate system may be converted to an initial ultrasonic image of a rectangular coordinate system.

Some embodiments of the present disclosure may directly store the control instructions (e.g., emitting instructions, gaining instructions, receiving instructions and/or idle instructions) in any position in the ring buffer in any order, and may take the specified control instructions from the ring buffer for execution based on the storage position of the control instructions, to avoid frequent memory allocation and release, thus to reduce system overhead and memory fragments, to improve the operation efficiency of the system.

FIG. 9 is a flowchart illustrating an exemplary process for determining a focus position corresponding to each emission of ultrasonic waves according to some embodiments of the present disclosure.

In some embodiments, each ultrasonic image may be obtained based on scanning data corresponding to the plurality emissions. In the plurality of emissions, each ultrasonic wave may correspond to a focus when the ultrasonic wave is emitting, and the focus may be the intersection of the extension line of the ultrasonic beam of the corresponding ultrasonic wave emitted on the target object or a portion of the target object. It can be understood that the more the count of focuses corresponding to the target object or a portion of the target object are, that is, the more the ultrasonic beams emitted to the target object or a portion of the target object are, the higher the resolution of the ultrasonic image of the target object or a portion of the target object is.

Therefore, in order to compensate for the low resolution of the edge of the ultrasonic image caused by the energy loss on both sides of the ultrasonic probe, in the process of emitting ultrasonic waves to the target object, the focus trajectory of emitting ultrasonic waves with dense focuses on both sides may be designed. In addition, for the ultrasonic probe scanning the target object in a deep position, for example, for the convex array ultrasonic probe, a focus trajectory of emitting ultrasonic waves with dense middle focuses may be designed to improve the ultrasonic image resolution of the target object in the deep position.

As shown in FIG. 9, the method 900 for emitting ultrasonic waves may include one or more of the following operations.

In 910, a first relative position corresponding to each emission of the plurality of ultrasonic waves may be obtained based on emission times and/or an emission order of the plurality of ultrasonic waves, to obtain a plurality of first relative positions corresponding to a plurality of emissions of the plurality of ultrasonic waves.

Specifically, the operation 910 may be implemented by the first relative position determination sub-unit 510.

The plurality of ultrasonic waves may be a plurality of ultrasonic waves corresponding to each ultrasonic image. In some embodiments, the plurality of ultrasonic waves may be in a non-focused emission mode. The non-focused emission mode may refer to an emission mode in which a focus corresponding to an ultrasonic wave is not in an imaging area during emitting. For example, the non-focused emission mode may include at least one of a plane wave emission mode, a divergent wave emission mode, a wide beam emission mode, or the like.

The emission times of the plurality of ultrasonic waves may be emission times corresponding to each ultrasonic image. For example, if a count of emissions is 10, each ultrasonic image is generated based on the scanning data of reflected ultrasonic waves obtained from emitting 10 times of ultrasonic waves to the target object or a portion of the target object. In some embodiments, the first relative position determination sub-unit 510 may determine the count of emissions based on the ultrasonic examination mode input by the user (e.g., the belly examination mode, a vascular examination mode, a thyroid examination mode, etc.). For example, the first relative position determination sub-unit 510 may determine that the count of emissions is 10 based on the ultrasonic examination mode (e.g., "belly examination mode") input by the user. In some embodiments, the first relative position determination sub-unit 510 may also directly obtain the count of emissions input by the user.

The emission order of the plurality of ultrasonic waves may include an order of emissions of the plurality of ultrasonic waves. The order of emissions of the plurality of ultrasonic waves may be represented by numbers. For example, the emission order of 10 ultrasonic waves may be 0, 1, 2, . . . , 8 and 9, respectively, indicating the first emission of ultrasonic wave, the second emission of ultrasonic wave, the third emission of ultrasonic wave, . . . , the ninth emission of ultrasonic wave, and the tenth emission of ultrasonic wave.

The first relative positions may be relative positions of centers of array elements corresponding to the focuses of corresponding ultrasonic waves if the centers of array elements on the ultrasonic probe are distributed at equal intervals when the corresponding ultrasonic waves are emitted according to the emission order. The relative positions may refer to or include a position distribution in which the distances (i.e., the emission distances) from the centers of the array elements corresponding to the emission order to the center of the ultrasonic probe is mapped to a certain range. More descriptions of the emission distance may be found in the descriptions of operation 930.

Figure 10A:
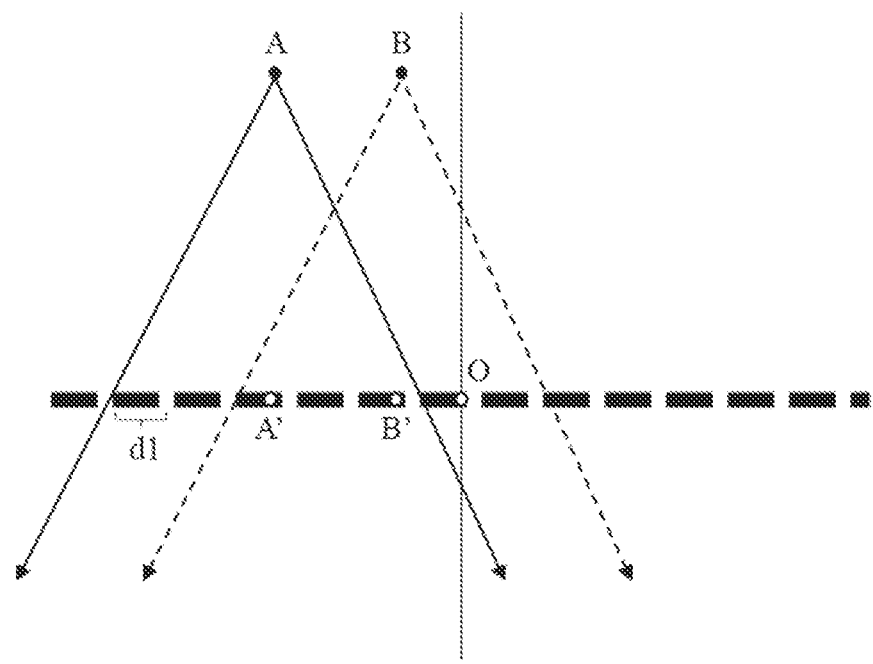
FIG. 10a is a schematic diagram illustrating an exemplary linear array ultrasonic probe transducer according to some embodiments of the present disclosure.

In some embodiments, the first relative position may be represented by a value between [−1,1]. As shown in FIG. 10a, if the ultrasonic probe is a linear array probe, the focuses corresponding to the plurality of emissions may include a focus A corresponding to the ultrasonic wave emitted in a first emission and a focus B corresponding to the ultrasonic wave emitted in a second emission, and the first relative position corresponding to the ultrasonic wave emitted in the first emission may be a distance A'O between a center A' of an array element corresponding to the focus A and a center O of the ultrasonic probe center, which is mapped to a value between [−1,1]. The first relative position corresponding to the ultrasonic wave emitted in the second emission may be a distance B'O between a center B' of an array element corresponding to the focus B and a center O of the ultrasonic probe center, which is mapped to a value between [−1,1]. For example, if the first relative position is less than 0, the first relative position may indicate that the focus of the ultrasonic wave corresponding to the emission order is on the left side of the center of the ultrasonic probe when emitting. If the first relative position is greater than 0, the first relative position may indicate that the focus of the ultrasonic wave corresponding to the emission order is on the right side of the center of the ultrasonic probe when emitting. Further, the closer the first relative position is to −1 or 1, the closer the focus of the ultrasonic wave corresponding to the emission order is to the edge of the ultrasonic probe; the closer the first relative position is to 0, the closer the focus of the ultrasonic wave corresponding to the emission order is to the center of the ultrasonic probe.

In some embodiments, the first relative position may also reflect the relative position of the corresponding energy distribution of the ultrasonic wave corresponding to the emission order in the ultrasonic image frame. For example, the closer the first relative position is to −1 or 1, the closer the energy distribution of the ultrasonic wave corresponding to the emission order in the ultrasonic image frame is to the edge of the ultrasonic image; the closer the first relative position is to 0, the closer the energy distribution of the ultrasonic wave corresponding to the emission order in the ultrasonic image frame is to the center of the ultrasonic image.

In some embodiments, the first relative position may be determined according to Equation (1):

$$\alpha_i = \frac{2 * i}{n - 1} - 1.0, \tag{1}$$

where n represents the count of emissions of the plurality of ultrasonic waves, i represents an emission order corresponding to each emission of the plurality of ultrasonic waves, i≥0, $\alpha_i$ represents the first relative position of the ultrasonic wave corresponding to the i-th emission, $\alpha_i \in [-1,1]$.

As shown in Equation (1), the first relative positions of the plurality of ultrasonic waves may be distributed at equal intervals of $$\frac{2}{n-1},$$

and the focuses corresponding to the plurality of ultrasonic waves may be distributed at equal intervals.

For example, if the count of emission times n of the plurality of ultrasonic waves is 10, the first relative positions of the plurality of ultrasonic waves corresponding to the first (i=0), second (i=1), third (i=2), . . . , ninth (i=8) and tenth (i=9) emissions are (−1), (−7/9), (−5/9), . . . , 7/9 and 1, respectively, which are distributed at equal intervals of 2/9.

It can be understood that based on the first relative positions and/or parameter(s) of the ultrasonic probe, the emission distances corresponding to the centers of the array elements distributed at equal intervals may be calculated, to further calculate the focus positions distributed at equal intervals. In some embodiments, the ultrasonic waves emitted based on the focus positions distributed at equal intervals may not solve the problem of uneven resolution distribution of the ultrasonic image caused by scattering from both sides of ultrasonic probe. Therefore, it is necessary to further obtain the emission distances corresponding to the centers of the array elements distributed at unequal intervals, to further calculate the focus positions distributed at unequal intervals.

In 920, the plurality of first relative positions distributed at equal intervals may be mapped to a plurality of second relative positions distributed at unequal intervals corresponding to the plurality of emissions.

Specifically, the operation 920 may be implemented by the second relative position determination sub-unit 520.

The second relative positions may be relative positions of the centers of the array elements on the ultrasonic probe corresponding to the focuses distributed at unequal intervals when the ultrasonic waves are emitted according to the emission order.

It can be understood that when a plurality of focuses corresponding to the plurality of ultrasonic waves are distributed at equal intervals, the plurality of ultrasonic waves are uniformly emitted from the ultrasonic probe. However, the closer the ultrasonic wave to the edge of the ultrasonic probe, the greater the energy loss, the lower the resolution at the position in the ultrasonic image frame (i.e., the edge position of the ultrasonic image frame).

In order to compensate for the uneven energy loss during the plurality of emissions, the second relative position determination sub-unit 520 may map focus relative positions distributed at equal intervals to unequal intervals. Specifically, the second relative position determination sub-unit 520 may set more focuses at the position where the ultrasonic energy loss is greater, making the intervals between the plurality of focus relative positions smaller.

In some embodiments, the second relative position determination sub-unit 520 may map a plurality of first relative positions distributed at equal intervals to a plurality of second relative positions distributed at unequal intervals corresponding to the plurality of emissions through a nonlinear curve.

In some embodiments, the nonlinear curve may be represented by Equation (2):

$$W_i = \frac{1}{2}\alpha_i(3-\alpha_i^2) \quad (2)$$

where i represents an emission order corresponding to emitting each of the plurality of ultrasonic waves, i≥0, $\alpha_i$ represents the first relative position of the ultrasonic wave corresponding to the i-th emission, $W_i$ represents the second relative position of the ultrasonic wave corresponding to the i-th emission.

Continuing with the above example, the second relative position determination sub-unit 520 may map the first relative positions −1, −7/9, −5/9, . . . , 5/9, . . . , 7/9, 7/9, and 1 corresponding to the 0th, 1st, 2nd, . . . , 7th, 8th and 9th emission to the second relative positions −1, −679/729, −545/729, . . . , 545/729, 679/729, and 1, respectively, through the curve expressed by Equation (2), with intervals of 50/729, 134/729, . . . , 134/729 and 50/729.

According to the Equation (2), the closer the second relative position is to −1 or 1 (i.e., the closer the focus of the ultrasonic wave corresponding to the emission order is to the edge of the ultrasonic probe), the smaller the intervals between the corresponding second relative positions are, the greater the density of corresponding focus distribution is. The closer the second relative position is to 0 (that is, the closer the focus of the ultrasonic wave corresponding to the emission order is to the center of the ultrasonic probe), the greater the intervals between the corresponding second relative positions are, and the smaller the density of the corresponding focus distribution is.

Similar to the first relative position, the second relative position may also reflect the relative position of the corresponding energy distribution of the ultrasonic wave corresponding to the emission order in the ultrasonic image frame. For example, the closer the second relative position is to −1 or 1, the closer the corresponding energy distribution of the ultrasonic wave corresponding to the emission order in the ultrasonic image frame is to the edge of the ultrasonic image. The closer the second relative position is to 0, the closer the corresponding energy distribution of the ultrasonic wave corresponding to the emission order in the ultrasonic image frame is to the center of the ultrasonic image.

Some embodiments of the present disclosure show that the plurality of first relative positions distributed at equal intervals may be mapped to a plurality of second relative positions distributed at unequal intervals corresponding to the plurality of emissions through a curve, so that the relative positions between the plurality of focuses corresponding to the plurality of ultrasonic waves have a greater distribution density on both sides of the ultrasonic probe, to compensate for the low resolution caused by the energy loss on both sides of the ultrasonic probe of the edge of the ultrasonic image.

In 930, an emission distance and a focus radius corresponding to each of the plurality of emissions may be determined based on an emission parameter and/or a second relative position corresponding to each emission.

Specifically, the operation 930 may be implemented by the focus radius determination sub-unit 530.

The emission parameter may be a parameter configured to control emission. In some embodiments, the emission parameter may include a count of channels of the transducer, an array element width, and/or a curvature of the transducer.

The count of channels of the transducer may be a count of channels (control circuit) of the transducer. In some embodiments, each channel of the transducer may excite one array element. For example, if the count of channels of the transducer is 20, then 20 array elements may be excited.

Figure 10B:
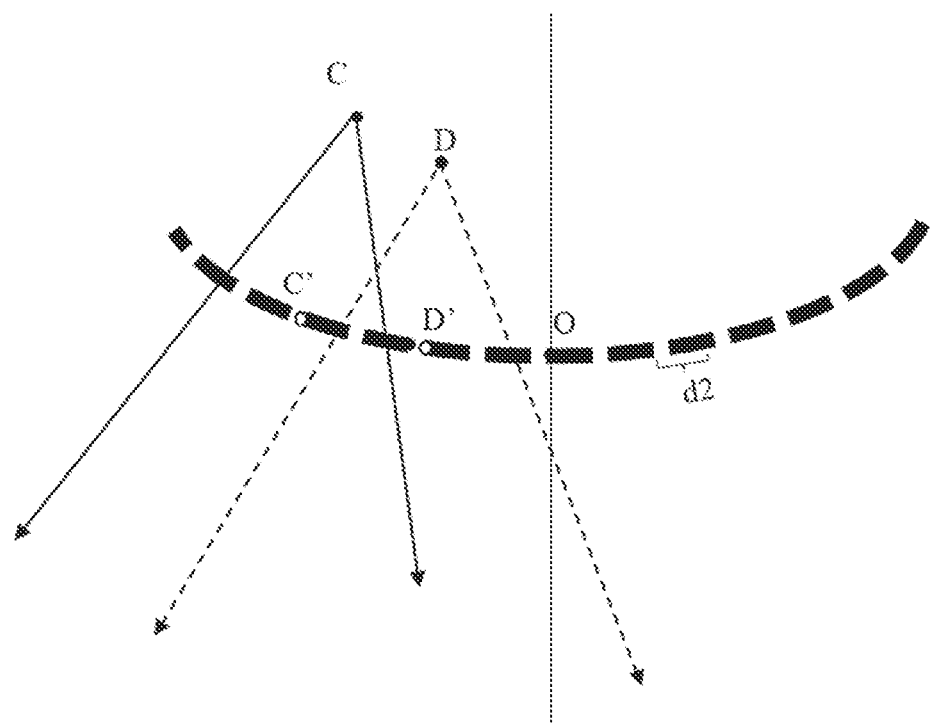
FIG. 10b is a schematic diagram illustrating an exemplary convex array ultrasonic probe transducer according to some embodiments of the present disclosure.

The array element width may be a cross-sectional width of the array element. As shown in FIG. 10*a*, the array element width of the transducer of the linear array ultrasonic probe (represented by a short black line segment in FIG. 10*a*) is d1 (e.g., 0.00003 m). As shown in FIG. 10*b*, the array element width of the transducer of the convex array ultrasonic probe (represented by a short black line segment in FIG. 10*b*) is d2 (e.g., 0.000452 m).

The curvature of the transducer may be a reciprocal of the radius of the transducer, which may represent a parameter of a bending degree of the array elements on the transducer.

The greater the curvature of the transducer is, the greater the bending degree of the array elements of the transducer is (i.e., the more convex the transducer is), and the smaller the radius of the transducer is. The smaller the curvature of the transducer, the smaller the bending degree of the array elements of the transducer is (i.e., the flatter the transducer is), and the larger the radius of the transducer is. As shown in FIG. 10a, if the array elements of the transducer of the linear array ultrasonic probe are arranged in a straight line, the curvature of the transducer of the linear array ultrasonic probe is 0. As shown in FIG. 10b, if the array elements of the transducer of the convex array ultrasonic probe are arranged in a curve, the curvature of the transducer of the convex array ultrasonic probe is greater than 0 (e.g., curvature k of the transducer is 20).

The emission distance may be a distance between the center of the array element and the center of the ultrasonic probe corresponding to the focus of the ultrasonic wave corresponding to the emission order.

As shown in FIG. 10a, if the ultrasonic probe is a linear array ultrasonic probe, a plurality of emission distances corresponding to the plurality of emissions may be represented by line segments A'O and B'O, where A'O represents the distance between a center A' of an array element corresponding to a focus A and a center O of the ultrasonic probe center, and B'O represents the distance between a center B' of an array element corresponding to a focus B and a center O of the ultrasonic probe center. As shown in FIG. 10b, when the ultrasonic probe is a convex array ultrasonic probe, the plurality of emission distances corresponding to the plurality of emissions may include arc length $\overset{\frown}{C'O}$ and $\overset{\frown}{D'O}$, where, $\overset{\frown}{C'O}$ represents a distance between a center C' of an array element corresponding to a focus C and the center O of the ultrasonic probe, $\overset{\frown}{D'O}$ represents a distance between a center D' of an array element and the center O of the ultrasonic probe corresponding to a focus D.

In some embodiments, the focus radius determination sub-unit 530 may determine the emission distance corresponding to each emission based on the count of channels of the transducer, the array element width and the second relative position corresponding to each emission.

In some embodiments, the focus radius determination sub-unit 530 may determine the emission distance corresponding to each emission based on Equation (3):

$$Phy_i = \frac{1}{2}(N-1) * D_s * W_i \qquad (3)$$

where N represents the count of channels of the transducer, $D_s$ represents the array element width, and $Phy_i$ represents the emission distance corresponding to the i-th emission.

Some embodiments of the present disclosure show that the plurality of emission distances with unequal intervals of the centers of the plurality of array elements corresponding to the plurality of focuses on the ultrasonic probe is obtained based on the plurality of second relative positions distributed at unequal intervals.

The focus radius may be a radius of a close tangent circle of the focus on the focus trajectory, which may reflect a bending degree of the focus trajectory. The larger the focus radius is, the smaller the bending degree of the corresponding focus at the focus trajectory is.

In some embodiments, the focus radius determination sub-unit 530 may determine the focus radius corresponding to each emission based on the emission distance corresponding to each emission, the second relative position corresponding to each emission, and/or the curvature of the transducer.

Specifically, the focus radius determination sub-unit 530 may determine a focus curvature corresponding to each emission based on the emission distance corresponding to each emission, the second relative position corresponding to each emission, and/or the curvature of the transducer.

The focus curvature may be a reciprocal of the focus radius. In some embodiments, the focus radius determination sub-unit 530 may determine the focus curvature corresponding to each emission based on Equation (4):

$$FK_i = \frac{\text{abs}(W_i)}{ConstK} - (1.0 - \text{abs}(W_i)) * k \qquad (4)$$

where i represents an emission order corresponding to each emission of the plurality of ultrasonic waves, $FK_i$ represents a focus curvature of an ultrasonic wave corresponding to the i-th emission, k represents the curvature of the transducer, ConstK represents an emission constant, wherein the ConstK may be adjusted based on experience, for example, the ConstK may be −0.04.

Further, the focus radius determination sub-unit 530 may determine whether the focus curvature corresponding to each emission is less than a curvature threshold.

It can be understood that the curvature k of the transducer of the linear array ultrasonic probe is 0. An absolute value of the corresponding focus curvature of each emission determined based on Equation (4) may be small, and a value of the corresponding focus radius may be large, resulting in that the corresponding focus position is outside a range of the linear array ultrasonic probe. The curvature threshold may be a minimum value of the focus curvature corresponding to each emission. For example, the curvature threshold may be 1.

If the absolute value of the focus curvature corresponding to a current emission order is less than the curvature threshold, the reciprocal of the curvature threshold is designated as the focus radius, and the direction of the focus radius may be determined based on the focus curvature. For example, the focus curvature $FK_1$ corresponding to the first emission is −0.5, the curvature threshold 1 is designated as the corresponding focus curvature, and the reciprocal 1 of the curvature threshold 1 is designated as the focus radius, and the direction of the focus radius may be determined as negative based on the corresponding focus curvature $FK_1$ (e.g., −0.5), that is, the focus radius $FR_1$ is −1.

If the absolute value of the focus curvature corresponding to the current emission order is greater than the curvature threshold, the reciprocal of the focus curvature is designated as the focus radius. For example, the focal curvature $FK_2$ corresponding to the second emission is −2, and the absolute value of the focal curvature $FK_2$ is 2, which is greater than the curvature threshold 1, the reciprocal −0.5 of focus curvature −2 is designated as the focus radius $FR_2$.

In some embodiments, the focus radius determination sub-unit 530 may determine the focus radius corresponding to each emission based on Equation (5):

$$FR_i = \begin{cases} \text{sgn}(FK_i)/a, & |FK_i| < a \\ 1/FK_i, & |FK_i| \geq a \end{cases} \qquad (5)$$

where i represents an emission order corresponding to each emission of the plurality of ultrasonic waves, $FR_1$ represents a focus radius of an ultrasonic wave corresponding to the i-th emission, a represent the curvature threshold, sgn($FK_i$) represents obtaining a sign of the $FK_i$.

Some embodiments of the present disclosure show that obtaining the focus radius based on the second relative position may make the value of the second relative position become greater, that is, the farther the second relative position is from the center of the ultrasonic probe, the greater the absolute value of the focus curvature is. Further, if the absolute value of the focus curvature is greater than the curvature threshold, the smaller the value of the corresponding focus radius is, and the smaller the intervals of the corresponding focus radiuses are, so that the abscissa and ordinate of the focus position determined in the operation 840 based on the focus radius and the emission distance are further related to the second relative position. Meanwhile, if the absolute value of the focus curvature is less than the curvature threshold (i.e., the transducer is a linear array transducer), the value of the focus radius may remain unchanged, so that only the abscissa of the focus position determined in the operation 940 based on the emission distance is further related to the second relative position.

In 940, the focus position corresponding to each emission may be determined based on the emission distance and the focus radius corresponding to the each of the plurality of emissions.

Specifically, the operation 940 may be implemented by the focus position determination sub-unit 540.

It can be understood that by determining the focus position corresponding to each emission, the focus trajectory of the plurality of ultrasonic waves may be determined.

In some embodiments, the focus position determination sub-unit 540 may obtain a radian corresponding to the emission distance corresponding to each emission based on the emission distance corresponding to each emission and the curvature of the transducer. Specifically, the radian corresponding to the emission distance corresponding to each emission may be a ratio of the emission distance $Phy_i$ corresponding to each ultrasonic emission to the radius of curvature of the transducer, that is, a product of the emission distance $Phy_i$ corresponding to each ultrasonic emission and the curvature k of the transducer, i.e., $Phy_i*k$.

Further, the focus position determination sub-unit 540 may obtain projection distances of the emission distance corresponding to each emission on a transversal axis and a longitudinal axis respectively based on the radian corresponding to the emission distance corresponding to each emission. Specifically, the focus position determination sub-unit 540 may obtain the projection distances $\sin(Phy_i*k)$ and $\cos(Phy_i*k)$ of the emission distance corresponding to each emission on a transversal axis and a longitudinal axis, respectively.

Further, the focus position determination sub-unit 540 may obtain an abscissa of the focus corresponding to each emission based on the projection distance of the emission distance corresponding to each emission on the transverse axis, the focus radius and/or the curvature of the transducer. And the focus position determination sub-unit 540 may obtain an ordinate of the focus corresponding to each emission based on the projection distance of the emission distance corresponding to each emission on the longitudinal axis, the focus radius and/or the curvature of the transducer.

In some embodiments, the focus position determination sub-unit 540 may determine the abscissa and the ordinate of the focus corresponding to each emission based on Equation (6):

$$fx_i = \frac{\sin(Phy_i*k)}{k} + FR_i * \sin(Phy_i*k) \qquad (6)$$

$$fz_i = \frac{\cos(Phy_i*k) - 1}{k} + FR_i * \cos(Phy_i*k)$$

where i represents an emission order corresponding to each emission of the plurality of ultrasonic waves, $fx_i$ and $fz_i$ represent the abscissa and the ordinate of the focus of the ultrasonic wave corresponding to the i-th emission, respectively, $FR_i$ represents a focus radius of an ultrasonic wave corresponding to the i-th emission.

When the ultrasonic probe is a linear array ultrasonic probe, and the corresponding curvature k of the transducer is 0, the focus trajectory of the plurality of ultrasonic waves is $$\begin{cases} fx_i = Phy_i \\ fz_i = FR_i \end{cases}.$$

It can be seen from the foregoing that the greater the absolute value of the second relative position corresponding to the emission order is (i.e., farther away from the center of the ultrasonic probe), the greater the absolute value of the corresponding emission distance with unequal intervals is, and the smaller the interval is, that is, the greater the absolute value of the abscissa is, the smaller the interval is. When the absolute value of the focus curvature is less than the curvature threshold (i.e., the transducer is a linear array transducer), the value of the focus radius may remain unchanged, which is the reciprocal 1/a of the curvature threshold. The direction of the focus radius may be determined based on the direction of the focus curvature, that is, the ordinate is sgn($FK_i$)1/a. As shown in FIG. 11a, the focuses farther away from the origin on the transversal axis (the X axis) is denser, the greater energy loss closer to both sides of the ultrasonic probe may be compensated. Meanwhile, the absolute value of the focus on the longitudinal axis (the Z axis) is close to 0.

If the ultrasonic probe is a convex array ultrasonic probe and the corresponding curvature of the transducer k≠0, the focus trajectory of the plurality of ultrasonic waves may be further related to the emission distance and the curvature of the transducer corresponding to each emission.

Figure 11B:
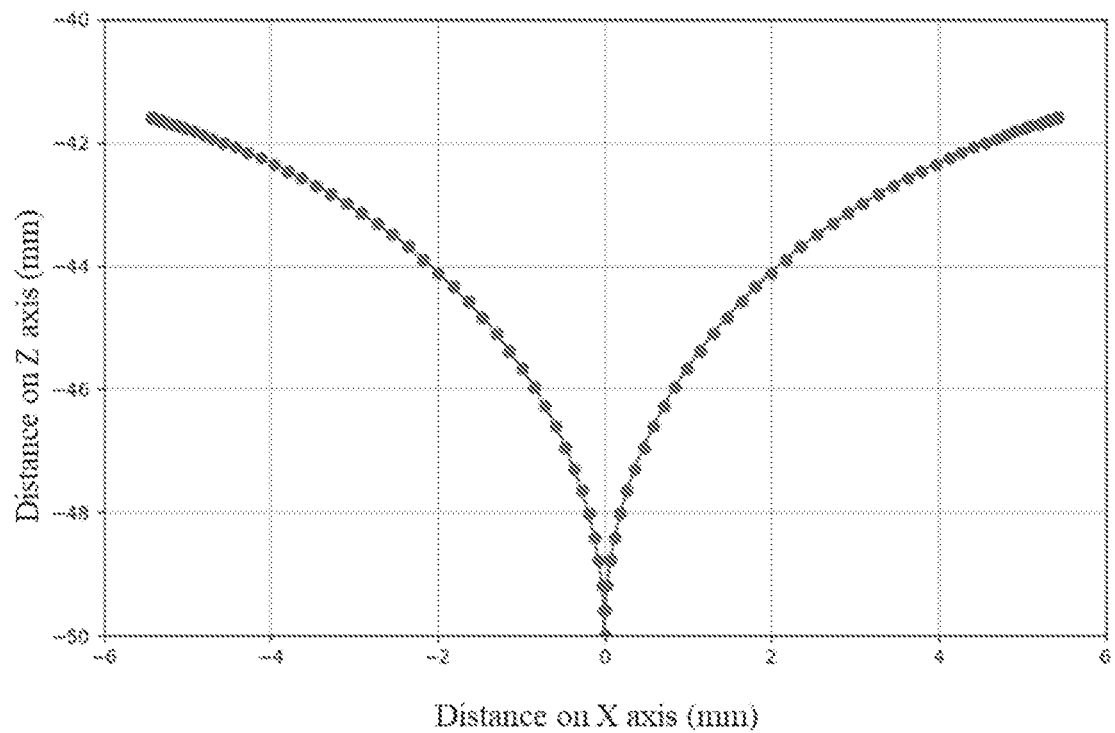
FIG. 11b is a schematic diagram illustrating an exemplary focus trajectory of ultrasonic emission of a convex array ultrasonic probe according to some embodiments of the present disclosure.

As shown in FIG. 11b, the denser the focuses closer to the origin or the focuses farther away from the origin on the transversal axis (or the X axis) are, the greater energy loss of the ultrasonic probe closer to both sides may be compensated, and the resolution of the ultrasonic image of the target object with the convex array ultrasonic probe being in the depth position may be improved. In addition, the closer the focuses on the transversal axis (or the X axis) are to the origin (i.e., the smaller the second relative positions are), the absolute value of the focuses on the longitudinal axis (or the Z axis) may be small.

Figure 12:
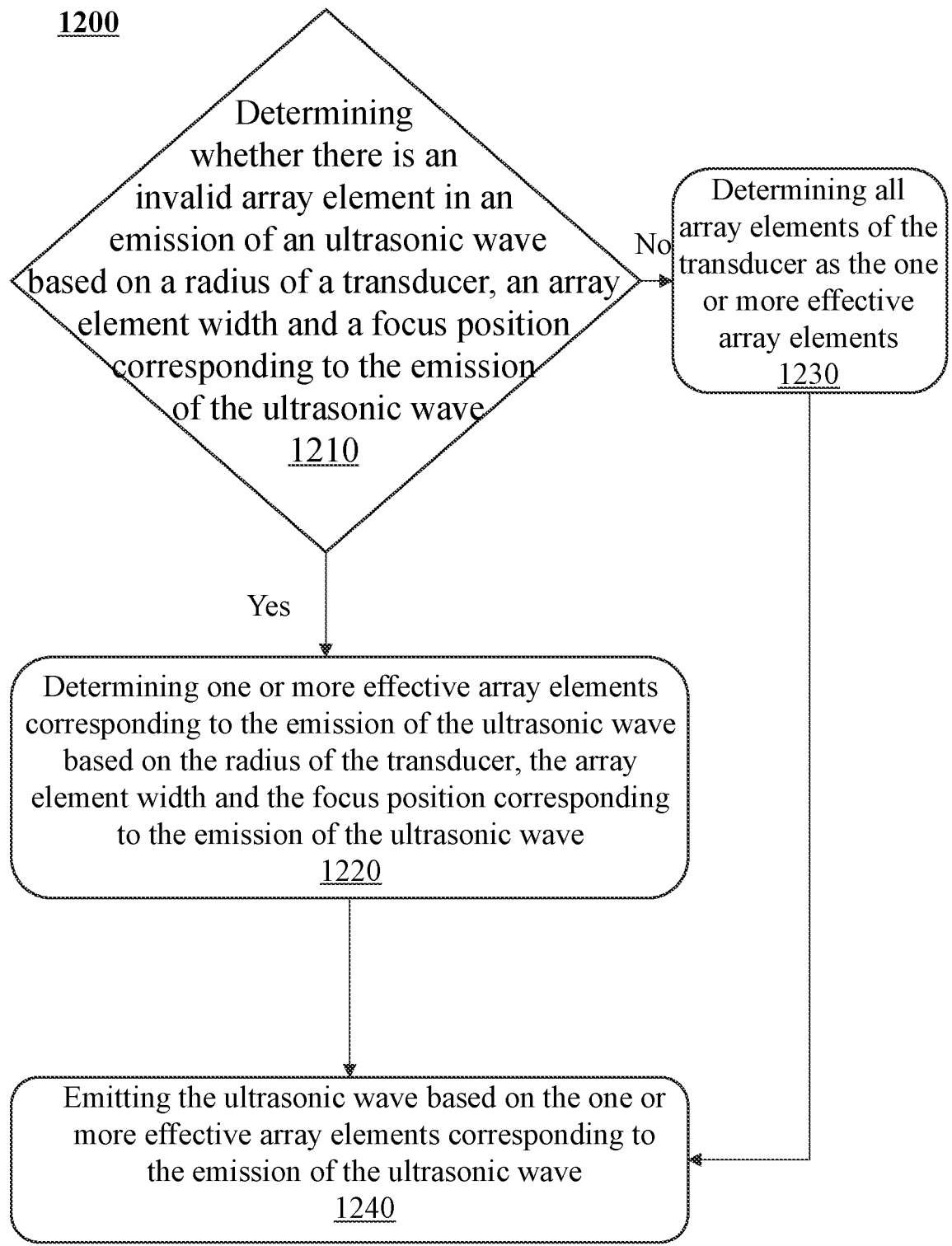
FIG. 12 is a flowchart illustrating an exemplary process for determining an effective array element corresponding to each emission of ultrasonic waves according to some embodiments of the present disclosure.

FIG. 12 is a flowchart illustrating an exemplary process for determining an effective array element corresponding to each emission of ultrasonic waves according to some embodiments of the present disclosure.

In addition to the energy loss on both sides of the ultrasonic probe, the ultrasonic wave may scatter in the process of propagation from the ultrasonic probe to the target object or a portion of the target object, so that some ultrasonic beams cannot reach the target object or a portion of the target object, resulting in energy loss and reducing the resolution of the ultrasonic image. Therefore, in order to enhance the ultrasonic energy reaching the target object, that is, to increase a count of ultrasonic beams emitted to the target object or a portion of the target object, the effective array element corresponding to each emission may be determined so that the ultrasonic beams emitted by each effective array element may reach the target object or a portion of the target object as much as possible.

As shown in FIG. 12, the method 1200 for determining the effective array element corresponding to each emission may include one or more of the following operations.

In 1210, whether there is an invalid array element in each emission may be determined based on a radius of a transducer, an array element width and/or a focus position corresponding to each emission.

Specifically, the operation 1210 may be implemented by the determination sub-unit 610.

The invalid array element may refer to an array element that the ultrasonic beams emitted by the array element cannot reach the target object or a portion of the target object. For example, if the ultrasonic beams emitted by array element a is scattered in the process of propagation, and the ultrasonic beams cannot reach the target object or a portion of the target object along the propagation direction after scattering, then the array element a may be an invalid array element.

In some embodiments, the determination sub-unit 610 may determine a maximum value of an array element pointing angle corresponding to the emission of the ultrasonic wave based on the array element width, and determine a maximum pointing circle corresponding to the maximum value of the array element pointing angle based on the radius of the transducer and the maximum value of the array element pointing angle.

According to properties of material of the ultrasonic probe, the array elements in the ultrasonic probe may have directivity, that is, the ultrasonic waves emitted by the array element may propagate along a specified direction. In some embodiments, the range of the specified direction may be represented by the array element pointing angle.

The array element pointing angle of the convex array ultrasonic probe may be an angle with a vertex of the array element, and one side of the angle may be a connecting line between the center of the transducer and the array element. The array element pointing angle may represent that a range of propagation direction of the ultrasonic beam emitted by the array element. For the convex array ultrasonic probe shown in FIG. 13a, the array element pointing angle corresponding to the array element a is an angle θ1 with array element a as the vertex, and the connecting line between the center P of the transducer and array element a as one side. The array element pointing angle corresponding to the array element a may represent that ultrasonic waves emitted by the array element a may propagate within the range of the angle θ1. It can be understood that another side of the array element pointing angle may be on the left and/or right side of the connecting line between the center of the transducer and the array element, and the array element pointing angle at different positions may correspond to different focus positions.

The array element pointing angle of the linear array ultrasonic probe may be an angle between the connecting line of the focus corresponding to emission and the array element and a central axis of the transducer. For the linear array ultrasonic probe shown in FIG. 13b, the array element pointing angle corresponding to array element c is the angle θ3 between the connecting line $F_tc$ of the focus $F_t$ corresponding to emission and the array element c and a central axis of the transducer. The array element pointing angle corresponding to array element c may represent that ultrasonic waves emitted by the array element c may propagate within the range of the angle θ3.

It can be understood that the smaller the array element pointing angle is, the better the directivity of the array element, and the less the ultrasonic waves are to diffract in the process of propagation. Therefore, in order to avoid acoustic wave aliasing and reduce the energy loss of ultrasonic wave in the process of propagation, to improve the energy when ultrasonic wave reaches the target object, the maximum value of array element pointing angle corresponding to emission needs to meet Equation (7):

$$\sin(|\theta|) = \lambda/2d \tag{7}$$

where θ represents the maximum value of array element pointing angle corresponding to emission, λ represents a wavelength of the ultrasonic wave, d represents the array element width of the ultrasonic probe.

The maximum pointing circle corresponding to the maximum value of the array element pointing angle of the convex array ultrasonic probe can be a circle with a center of the transducer as the center. And a radius of the maximum pointing circle may be a product of a sine value of the maximum value of the array element pointing angle and the radius of the transducer. At the time, another side of the array element pointing angle may be a tangent of the maximum pointing circle.

Figure 13A:
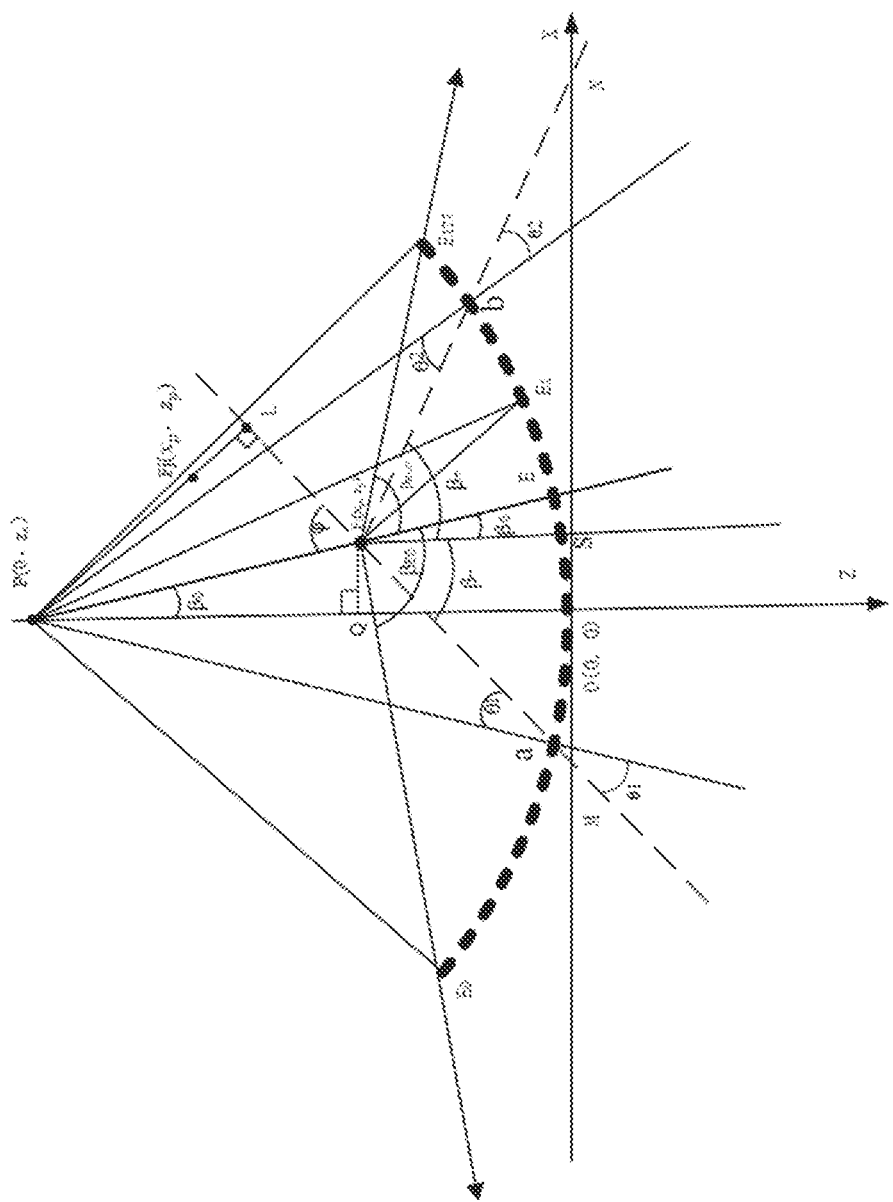
FIG. 13a is a schematic diagram illustrating determining exemplary effective array element of a convex array ultrasonic probe according to some embodiments of the present disclosure.

As shown in FIG. 13a, PL is a vertical line on an extension line Pa passing a point P. In a right triangle PLa, Pa is a hypotenuse, and a length of Pa is the radius of the transducer. PL is an opposite side corresponding to the array element pointing angle with the maximum value θ (assuming that θ1=θ), a length of PL is a product Rsinθ of a sine value of the maximum value of the array element pointing angle θ and the radius R of the transducer. It can be seen that PL is a radius of the maximum pointing circle corresponding to the maximum value θ (assuming that θ1=θ) of the array element pointing angle, that is, the maximum pointing circle corresponding to the maximum value θ (assuming that θ1=θ) of the array element pointing angle may be a circle with P as a center and PL as a radius.

Further, the determination sub-unit 610 may determine whether the focus position is within the maximum pointing circle, and in response to a determination that the focus position is within the maximum pointing circle, the determination sub-unit 610 may determine that there is no invalid array element in the emission of the ultrasonic wave; in response to a determination that the focus position is not within the maximum pointing circle, the determination sub-unit 610 may determine that there is an invalid array element in the emission of the ultrasonic wave.

In some embodiments, the determination sub-unit 610 may determine whether the focus position is within the maximum pointing circle by comparing a distance from the focus position to the center of the maximum pointing circle and the radius of the maximum pointing circle based on Equation (8):

$$\sqrt{x_p^2 + (z_R - z_p)^2} - R\sin\theta \leq 0 \tag{8}$$

where in a coordinate system with the central axis of the transducer as a longitudinal axis, and a center array element of the transducer as the origin, $x_p$ and $z_p$ represent an abscissa and an ordinate of the focus position, respectively, $z_R$ represents an ordinate of the center of the transducer, the absolute value of $z_R$ is the radius R of the transducer, $\sqrt{x_p^2+(z_R-z_p)^2}$ represents a distance from the focus position to the center of the maximum pointing circle.

When the focus position is within the maximum pointing circle, that is, Equation (8) is met, there may be no invalid array element in the plurality of emissions of the convex array ultrasonic probe. Further, the effective array element corresponding to the emission may be determined based on the operation 1230. As shown in FIG. 13a, the focus Fj is on the radius PL of the maximum pointing circle, and a length of PFj is less than the radius of the maximum pointing circle, the focus Fj meet Equation (8).

When the focus position is not within the maximum pointing circle, that is, Equation (8) is not met, there may be an invalid array element in the plurality of emissions of the convex array ultrasonic probe. Further, the effective array element corresponding to the emission may be determined based on the operation 1220. As shown in FIG. 13a, the focus Fi is on a tangent of the maximum pointing circle (i.e., the other side of the array element pointing angle with the maximum value), and a length of PFi is greater than the radius of the maximum pointing circle, the focus Fi does not meet Equation (8).

The linear array ultrasonic probe may be regarded as a convex array ultrasonic probe with the center of the transducer at infinity, that is, the radius R of the transducer is infinity. The effective array element corresponding to the emission may be determined directly based on the operation 1220.

In 1220, in response to an existence of the invalid array element in the emission, determining the one or more effective array elements corresponding to each emission based on the radius of the transducer, the array element width and/or the focus position corresponding to each emission.

Specifically, the operation 1220 may be implemented by the determination sub-unit 620.

The ultrasonic beams emitted by the effective array element may reach the target object or a portion of the target object. For example, if the ultrasonic beams emitted by array element a have scattered during propagation, but the ultrasonic beams still reach the target object or a portion of the target object along the scattered direction during propagation, the array element a may be an effective array element.

In some embodiments, the determination sub-unit 620 may determine a first deflection angle based on the radius of the transducer and/or the focus position. The first deflection angle may be an angle between a connecting line of a center of the transducer and the focus position and a central axis of the transducer.

As shown in FIG. 13a, the angle $\beta_0$ between a connecting line PFi of a center P of the transducer of the convex array ultrasonic probe and the focus position Fi and a central axis PO of the transducer is the first deflection angle. In the right triangle PQFi, the point Q is the foot point of the focus Fi on the central axis PO, and the determination sub-unit 620 may determine the first deflection angle $\beta_0$ based on an opposite side QFi of the angle $\beta_0$ and an adjacent side PQ of the angle $\beta_0$ in the right triangle PQFi. The value of opposite side QFi may be a difference between the radius of transducer and the ordinate of the focus position, and the value of the adjacent side PQ may be the abscissa of the focus position.

In some embodiments, the determination sub-unit 620 may obtain the first deflection angle $\beta_0$ based on Equation (9):

$$\beta_0 = \arctan\left(\frac{x_p}{z_R - z_p}\right) \qquad (9)$$

Figure 13B:
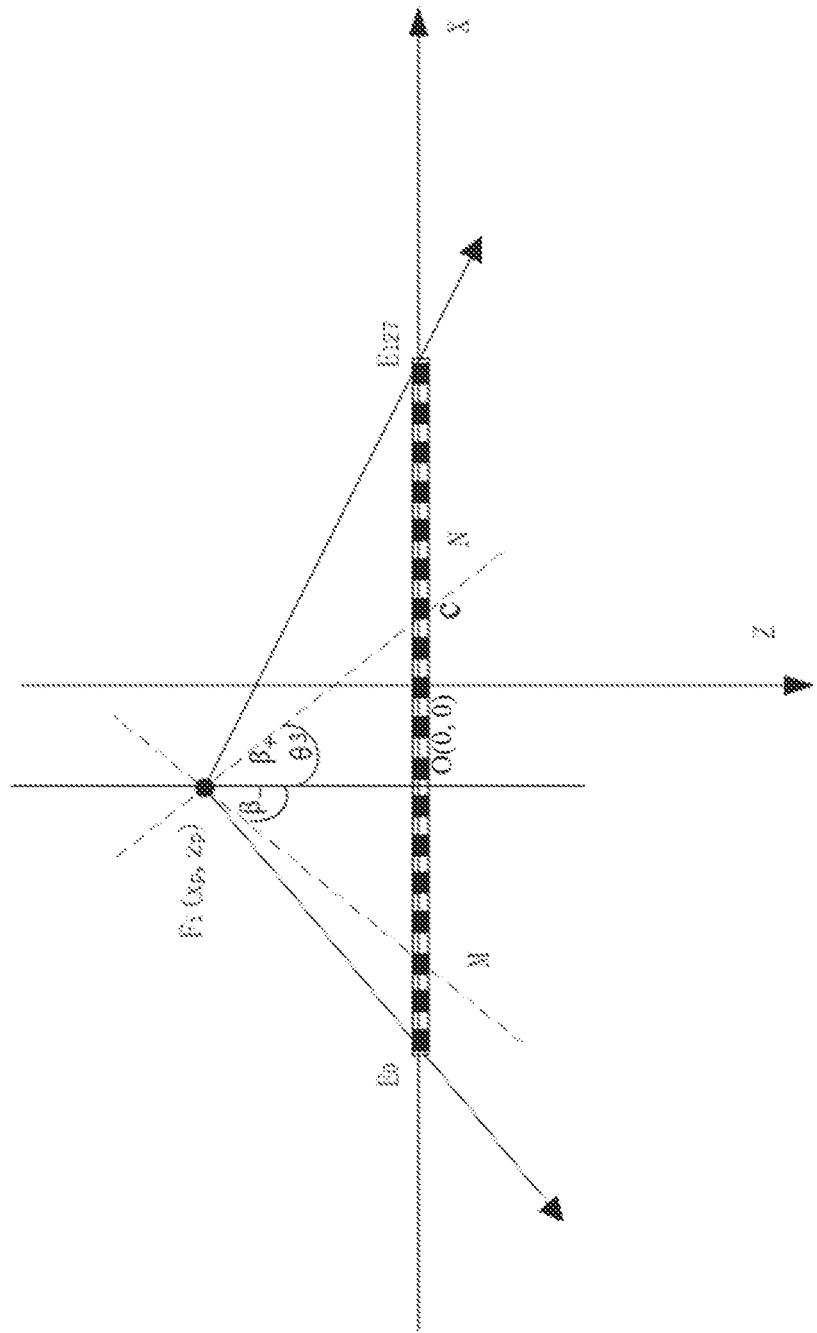
FIG. 13b is a schematic diagram illustrating determining exemplary effective array element of a linear array ultrasonic probe according to some embodiments of the present disclosure.

As shown in FIG. 13b, if the center P of the transducer of the linear array ultrasonic probe approaches infinity, and the radius of the transducer approaches infinity, the angle between a connecting line PFi of a center P of the transducer of the linear array ultrasonic probe and the focus position Fi and a central axis PO of the transducer may be 0°, that is, the first deflection angle may be 0°.

In some embodiments, the determination sub-unit 620 may determine a second deflection angle based on the maximum pointing circle, the transducer radius, and/or the focus position. The second deflection angle may be an angle between the connecting line of the center of the transducer and the focus position and a tangent of the maximum pointing circle passing through the focus position.

For the convex array ultrasonic probe shown in FIG. 13a, E is an intersection of the connecting line PFi between the center P of the transducer and the focus position Fi and the abscissa, and the second deflection angle φ is the angle between the connecting line PFi and the tangent aL of the maximum pointing circle passing through the focus position, $\angle$aFiE=$\angle$PFiL. In the right triangle PLFi, the determination sub-unit 620 may determine the second deflection angle φ based on the opposite side PL and the adjacent side PFi of $\angle$PFiL (i.e., φ) in the right triangle PLFi. The value of opposite side PL is the radius of the maximum pointing circle, and the value of adjacent side PFi is the distance from the focus position to the center of the transducer.

In some embodiments, the determination sub-unit 620 may determine the second deflection angle φ based on Equation (10):

$$\varphi = \arctan\frac{PL}{\sqrt{PF_i^2 - PL^2}} = \arctan\frac{R\sin(\theta)}{\sqrt{x_p^2 + (z_R - z_p)^2 - (R\sin(\theta))^2}} \qquad (10)$$

For the linear array ultrasonic probe shown in FIG. 13b, if the radius R of the transducer in Equation (10) is regarded as approaching infinity, the second deflection angle φ may be determined based on Equation (11):

$$\varphi = \lim_{R\to\infty} \arctan\frac{\sin\theta}{\sqrt{\left(\frac{x_p}{R}\right)^2 + \left(\frac{z_p}{R}-1\right)^2 - (\sin\theta)^2}} = \arctan\frac{\sin\theta}{\sqrt{1-\sin^2\theta}} = \theta \qquad (11)$$

Therefore, the second deflection angle of the linear array ultrasonic probe may be equal to the maximum value θ of the array element pointing angle of the convex array ultrasonic probe.

In some embodiments, the determination sub-unit 620 may determine a first slope of a first connecting line between the focus position and an initial left boundary effective array element based on a difference between the first deflection angle and the second deflection angle.

In the coordinate system with the central axis of the transducer as the ordinate, the initial left boundary effective array element may be a leftmost effective array element in a corresponding emission. It can be understood that the array elements on the left side of the initial left boundary may all be invalid elements.

The convex array ultrasonic probe shown in FIG. 13*a*, the value of θ1 is the maximum value of the array element pointing angle, and array element a is the initial left boundary effective array element, then all array elements on the left side of array element a are invalid array elements.

The first connecting line between the focus position and the initial left boundary effective array element may be a left boundary line dividing the initial left boundary effective array element. As shown in FIG. 13*a*, Fia is the first connecting line between the focus position Fi and the initial left boundary effective array element a.

The first slope is a slope of the first connecting line. In some embodiments, the determination sub-unit 620 may obtain the first slope based on an angle between the first connecting line and the longitudinal axis. As shown in FIG. 13*a*, S is the foot point of the focus Fi on the transversal axis, FiS is parallel to the Y axis, and a sine of the angle β (i.e., ∠aFiS) between the first line Fia and the line FiS is the first slope, where a value of the angle β (i.e., ∠aFiS) may be obtained based on a difference of the second deflection angle ∠aFiE and ∠SFiE (i.e., $\beta_{F0}$). The triangle SFiE may be similar to the triangle OPFi, and the value of LSFiE may be equal to the first deflection angle.

In some embodiments, the determination sub-unit 620 may determine the first slope of the first connection line based on Equation (12):

$$k_1 = \tan(\beta) = \tan(\beta_0 - \varphi) \tag{12}$$

In some embodiments, the determination sub-unit 620 may determine a second slope of a second connecting line between the focus position and an initial right boundary effective array element based on a sum of the first deflection angle and the second deflection angle.

Similar to the initial left boundary effective array element, in the coordinate system with the central axis of the transducer as the ordinate, the initial right boundary effective array element may be a rightmost effective array element corresponding to emission. It can be understood that the elements on the right side of the initial right boundary effective element may all be invalid elements. As shown in FIG. 13*a*, the value of θ2 is the maximum value of the array element pointing angle. If the array element b is the initial right boundary effective array element, all the array elements on the right side of the array element b are invalid array elements.

The second connecting line between the focus position and the initial right boundary effective array element may be the right boundary line dividing the initial right boundary effective array element. As shown in FIG. 13*a*, Fib is the second connecting line between the focus position Fi and the initial right boundary effective array element b.

The second slope is the slope of the second connecting line. In some embodiments, the determination sub-unit 620 may determine a second slope based on an angle between the second connecting line and the longitudinal axis. As shown in FIG. 13*a*, a sine of the angle $\beta_+$ between the second connecting line Fib and the connecting line FiS is the second slope, where a value of $\beta_+$ (i.e., ∠bFiS) may be obtained based on the sum of the second deflection angle ∠bFiE and the first deflection angle ∠SFiE.

In some embodiments, the determination sub-unit 620 may determine the second slope of the second connecting line based on Equation (13):

$$k_2 = \tan(\beta_+) = \tan(\beta_0 + \varphi) \tag{13}$$

The linear array ultrasonic probe as shown in FIG. 13*b*, the first deflection angle $\beta_0$ is 0, the second deflection angle is equal to the maximum value θ of the array element pointing angle, thus the first slope of the first connecting line $k_1 = \tan(\beta) = \tan(\beta_- - \varphi) = -\theta$, the second slope of the second connecting line $k_2 = \tan(\beta_+) = \theta$.

Further, the determination sub-unit 620 may obtain the left boundary effective array element and the right boundary effective array element based on the first slope, the second slope, the radius of the transducer and/or the boundary of all array elements.

Specifically, the determination sub-unit 620 may determine a position of the initial left boundary effective array element and/or a position of the initial right boundary effective array element based on the first slope, the second slope and/or the radius of the transducer. The position of the initial left boundary effective array element and/or the position of the initial right boundary effective array element may meet an array element directivity restriction condition. The array element directivity restriction condition may be that the array element pointing angles corresponding to the initial left boundary effective array element and/or the initial right boundary effective array element respectively are (or not greater than) the maximum value of the array element pointing angle, that is, the position of the initial left boundary effective array element and the position of the initial right boundary effective array element are on the first connecting line and the second connecting line respectively.

In addition, a distance from the position of the initial left boundary effective array element and/or the position of the initial right boundary effective array element of the convex array ultrasonic probe to the center of the transducer may be the radius of the transducer. In some embodiments, the determination sub-unit 620 may determine the position of the initial left boundary effective array element and/or the position of the initial right boundary effective array element of the convex array ultrasonic probe based on Equation (14):

$$\begin{cases} z - z_p = k_1(x - x_p) \\ z - z_p = k_2(x - x_p) \\ x^2 + (z_R - z_p)^2 = R^2 \end{cases} \tag{14}$$

where x and z are the abscissa and the ordinate of the position of the initial left boundary effective array element and/or the position of the initial right boundary effective array element, respectively.

The position of the initial left boundary effective array element and/or the position of the initial right boundary effective array element of the linear array ultrasonic probe may be on the X axis. In some embodiments, the determination sub-unit 620 may determine an ordinate of the initial left boundary effective array element and/or the initial right boundary effective array element of the linear array ultrasonic probe based on Equation (15):

$$\begin{cases} z - z_p = -k_1 x_p \\ z - z_p = -k_2 x_p \end{cases} \tag{15}$$

Two intersections of the first connecting line, the second connecting line and array element array of the transducer may be obtained based on Equation (14) or Equation (15), to further obtain the initial left boundary array element and/or the initial right boundary array element where the two intersections are located.

The left boundary effective array element and the right boundary effective array element may be the leftmost effective array element and the rightmost effective array element corresponding to the emission on the transducer, respectively. It can be understood that the initial left boundary effective array element and the initial right boundary effective array element that meet the array element directivity restriction condition may exceed the boundary of all the array elements on the transducer, that is, they may be located outside the transducer. Therefore, the determination sub-unit 620 may need to further determine whether the position of the initial left boundary effective array element and/or the position of the initial right boundary effective array element are within the boundary of all array elements.

Specifically, in response to a determination that the position of the initial left boundary effective array element and/or the position of the initial right boundary effective array element are within the boundary of all array elements, the determination sub-unit 620 may designate the initial left boundary effective array element and/or the initial right boundary effective array element as the left boundary effective array element and/or the right boundary effective array element, respectively. For example, if the transducer includes 128 elements, the boundary of all elements is between element E0 and element E127, and the position of the initial left boundary effective array element a is between element E0 and element E127, then the initial left boundary effective element a is designated as the left boundary effective element.

In contrast, in response to a determination that the position of the initial left boundary effective array element and/or the position of the initial right boundary effective array element is not within the boundary of all array elements, the determination sub-unit 620 may designate one or more array elements at the boundary of all array elements as the left boundary effective array element and/or the right boundary effective array element. Continuing with the above example, if the position of the initial right boundary effective array element b is outside the array element E0 and the array element E127, the array element E127 at the boundary of all the array elements is designated as the right boundary effective array element.

Then, a count of elements that may be included between the left boundary effective array element and the right boundary effective array element may be obtained based on a count of the left boundary elements and/or the right boundary elements. The count of array elements may be used as a size of an emission aperture when emitting ultrasonic waves. For example, the effective array element of the transducer may include all array elements from array element a (e.g., E27) to array element E127, then the corresponding size of emission aperture is 100.

For a focus position corresponding to an emission, when the focus position changes, the first deflection angle $\beta_0$, the second deflection angle $\varphi$ and/or the focus position may change, and the position of the left boundary effective array element and/or the position of the right boundary effective array element may change accordingly, so the calculated size of the emission aperture may change, that is, the corresponding size of the emission aperture may be dynamically calculated each time when emitting the ultrasonic waves.

In 1230, in response to an absence of the invalid array element in each emission, all array elements of the transducer may be determined as the one or more effective array elements.

Specifically, the operation 1230 may be implemented by the determination sub-unit 620.

As shown in FIG. 13*a*, if there is no invalid array element on the transducer, the determination sub-unit 620 may determine all the array elements of the transducer, such as all the array elements between E0 and E127 above, as effective array elements.

In 1240, the ultrasonic wave may be emitted based on the one or more effective array elements corresponding to the emission of the ultrasonic wave.

Specifically, the operation 1240 may be implemented by the emission module 320.

More descriptions for emitting the ultrasonic wave(s) based on the one or more effective array elements corresponding to the emission of the ultrasonic wave(s) may be found in the descriptions of operation 720.

Some embodiments of the present disclosure show that the size of effective array element (or effective aperture) may be calculated based on the array element directivity, which may improve the influence of acoustic grating lobe and reduce the energy loss of ultrasonic in the emission process, so as to improve the image quality of ultrasonic image and improve the utilization efficiency of array element resources.

FIG. 14 is a flowchart illustrating an exemplary process for transmitting a pulse according to some embodiments of the present disclosure. Specifically, FIG. 14 may be implemented by the pulse acquisition unit 430.

As shown in FIG. 14, a process 1400 for transmitting a pulse may include one or more of the following operations.

In 1410, at least one portion of the pulses of the plurality of ultrasonic waves may be divided into a transmission group.

The plurality of ultrasonic waves may be emitted based on an electrical signal including a plurality of pulses. Each pulse may indicate that the electrical signal is at least one of a "positive value", a "negative value" or "zero" in a unit time, which may indicate "exciting an array element with positive pressure", "exciting an array element with negative pressure" and "not exciting the array element" respectively, making the array element produce different vibration, to produce ultrasonic waves with different frequencies and sizes. In some embodiments, the numbers "0", "1" and "2" may be used to represent the "positive value", the "negative value" and "zero", respectively. For example, a plurality of pulses may include: 1, 0, 2, 2, 1, 1, 2, 0, 0, 1, . . . , in total of 100 pulses.

The transmission group may be a basic transmission form of transmitting pulses to the ultrasonic probe.

In some embodiments, each transmission group (or pulse group) may include a fixed count of pulses, that is, each pulse group may include the same count of pulses. For example, the pulse acquisition unit 430 may divide each N pulses of the plurality of pulses into a transmission group, that is, each transmission group may include N pulses, where In some embodiments, the pulse acquisition unit 430 may determine the count of pulses contained in each pulse group based on the total count of pulses. For example, if the total count of pulses is 99, N may be 3, and the pulse acquisition unit 430 may divide 99 pulses into 33 transmission groups. For another example, if the total count of pulses is 100, N may be 5, and the pulse acquisition unit 430 may divide 100 pulses into 20 transmission groups. Alternatively, N may be 4, and the pulse acquisition unit 430 may divide 100 pulses into 25 transmission groups.

In some embodiments, the pulse acquisition unit 430 may also determine the count of pulses included in each pulse group based on the transmission efficiency. More descriptions for determining the count of pulses contained in each pulse group based on the transmission efficiency may be found in the descriptions of 1320.

In some embodiments, each transmission group (or pulse group) may also include a different count of pulses. For example, the pulse acquisition unit 430 may determine that each transmission group contains N pulses based on the transmission efficiency, that is, each N pulses of the plurality of pulses are divided into one transmission group, and the remaining pulses are divided into one or more transmission groups. For example, the total count of pulses is 98, and the pulse acquisition unit 430 determines that N is 4 based on the transmission efficiency. The pulse acquisition unit 430 may divide 98 pulses into 24 transmission groups containing 4 pulses and 1 transmission group containing 2 pulses, or 23 transmission groups containing 4 pulses and 2 transmission groups containing 3 pulses.

In 1420, the transmission group may be compressed into compressed data, and the compressed data may be transmitted.

Compression may be a mechanism to reduce an amount of data through a specific algorithm. The compressed data may be a compressed transmission group. An amount of compressed data may be less than an amount of the transmission group.

In some embodiments, the pulse acquisition unit 430 may compress a transmission group into a value (i.e., the compressed data). As mentioned above, each pulse in each transmission group may correspond to at least one of a "positive value", a "negative value" and "zero", that is, each pulse may be one of three states, and then N pulses may be one of $3^N$ states (that is, each transmission group may be one of three states).

In some embodiments, the pulse acquisition unit 430 may represent any of the $3^N$ states corresponding to each transmission group with 3N values. For example, if N=4, $3^4$ values (such as 1~81) may be used to represent one of the 81 states corresponding to each transmission group. For example, 1 may correspond to a transmission group (0, 0, 0, 0), 2 may correspond to a transmission group (0, 0, 0, 1), 3 may correspond to a transmission group (0, 0, 1, 0), and 81 may correspond to a transmission group (2, 2, 2, 2).

Figure 15:
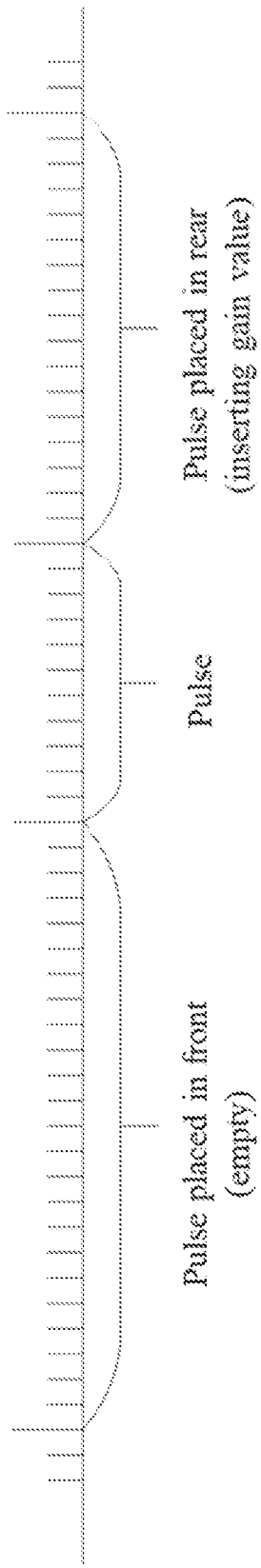
FIG. 15 is a schematic diagram illustrating inserting a gain value in the pulse according to some embodiments of the present disclosure.

In some embodiments, each pulse group may also include C state values. In some embodiments, the C state values may include gain values. As shown in FIG. 15, the pulse group placed in front and/or the pulse group placed in rear (that is at an empty state) may be used to insert a gain value. More descriptions of the gain value may be found in FIG. 16 and its related descriptions.

Accordingly, the pulse acquisition unit 430 may represent any of the $3^N+C$ states corresponding to each transmission group with $3^N+C$ values. In some embodiments, each state value may represent parameters such as T/R switching of the transducer, controlling gain changes, and/or recording system errors.

In some embodiments, the compressed data corresponding to each transmission group may be determined based on Equation (16):

$$x=3^{N-1}s_0+3^{N-2}s_1+\ldots 3^1 s_{N-2}+3^0 s_{N-1}+c \tag{16}$$

where $s_0, s_1, \ldots, s_{N-2}, s_{N-1}$ represent one of the three states corresponding to N pulses in the transmission group respectively, which may be represented by a value of $\{0,1,2\}$; c represents one of the C state values; x represents the compressed data corresponding to the transmission group.

For example, N=4, C=2, a value of c is 0 or 1, indicating that the transducer is switched to T mode or R mode respectively, then 100 pulses may be divided into: (1, 0, 2, 2), (1, 1, 2, 0), (0, 1, . . . ), . . . , each pulse group may be compressed into one of $3^4+2$ pieces of compressed data, and the compressed data obtained by compressing the first transmission group (1, 0, 2, 2) is $x_1=3^3 s_0+3^2 s_1+3^1 s_2+3^0 s_3+c=27\times 1+9\times 0+3\times 2+1\times 2+0=35$, the compressed data obtained by compressing the second transmission group (1, 0, 2, 0) is $x_2=3^3 s_0+3^2 s_1+3^1 s_2+3^0 s_3+c=27\times 1+9\times 1+3\times 2+1\times 0+1=43$; . . .

For another example, N=5, C=4, and a value of c is one of 1, 2, 3 and 4, which represent (when the transducer is switched to T mode, the system has no error), (when the transducer is switched to T mode, the system has an error), (when the transducer is switched to R mode, the system has no error), and (when the transducer is switched to R mode, the system has an error), respectively. Then 100 pulses may be divided into: (1, 0, 2, 1), (1, 2, 0, 0, 1), . . . , each pulse group may be compressed into one of $3^{5+4}$ pieces of compressed data. The compressed data obtained by compressing the first transmission group (1, 0, 2, 2, 1) is $x_1=3^4 s_0+3^3 s_1+3^2 s_2+3^1 s_3+3^0 s_4+c=81\times 1+27\times 0+9\times 2+3\times 2+1\times 1+4=110$, the compressed data obtained by compressing the second transmission group (1, 2, 0, 0, 1) is $x_2=3^4 s_0+3^3 s_1\ 3^2 s_2+3^1 s_3+3^0 s_4+c=81\times 1+27\times 2+9\times 0+3\times 0+1\times 1+3=119$; . . .

In some embodiments, the pulse acquisition unit 430 may determine a size of the compressed data based on the $3^N+C$ states corresponding to each transmission group. Specifically, each byte may represent 2 states, then the pulse acquisition unit 430 may round up based on $\log_2(3^N+C)$, thus the compressed data corresponding to $3^N+C$ states may be obtained.

For example, N=4, C=2, then a size of the compressed data corresponding to each transmission group is rounding up based on $\log_2(3^4+2)$, that is, 7 bits. For another example, N=5, C=4, then a size of the compressed data corresponding to each transmission group is rounding up based on $\log_2(3^5+4)$, that is, 8 bits.

As described above, the pulse acquisition unit 430 may also determine a count of pulses contained in each pulse group based on the transmission efficiency. For example, the pulse acquisition unit 430 may determine that the count of pulses contained in each pulse group is 5 based on the highest transmission efficiency when the size of the compressed data is 8 bits.

Further, the pulse acquisition unit 430 may transmit the compressed data corresponding to a plurality of transmission groups to the ultrasonic probe 110 through the network 140. For example, the pulse acquisition unit 430 may transmit the compressed data 110, 119, . . . , corresponding to the transmission group (1, 0, 2, 2, 1), (1, 2, 0, 0, 1), . . . , respectively, to the ultrasonic probe 110.

In 1430, the compressed data may be decoded to obtain the at least one portion of the pulses.

Decoding may be a process of restoring the compressed data received by the ultrasonic probe to the corresponding transmission group. Specifically, the pulse acquisition unit 430 may decode the received compressed data based on the received compressed data and the compression algorithm. In some embodiments, the transmission group corresponding to each compressed data may be determined based on Equation (17):

$$s_k=[(x-C)/3^{(N-1-k)}]\%\ 3 \tag{17}$$

where $s_k$ represents a corresponding state value in the transmission group, a value of $s_k$ is one of $\{0, 1, 2\}$, a value of k is [0, N−1], N represents a count of pulses in each transmission group.

For example, the compressed data $x_1=110$, based on that N=5, C=4, a corresponding state value in the transmission group $$s_0 = \left[\frac{106}{81}\right]\%3 = 1,$$

$$s_1 = \left[\frac{106}{27}\right]\%3 = 0,$$

$$s_2 = \left[\frac{106}{9}\right]\%3 = 2,$$

$$s_3 = \left[\frac{106}{3}\right]\%3 = 2,$$

$$s_4 = \left[\frac{106}{1}\right]\%3 = 1$$

may be obtained, that is, a corresponding transmission group (1, 0, 2, 2, 1) may be obtained.

Further, the pulse acquisition unit 430 may obtain the at least one portion of the pulses based on a plurality of transmission groups.

FIG. 16 is a flowchart illustrating an exemplary process for obtaining a gain value of ultrasonic echo signal according to some embodiments of the present disclosure.

Specifically, FIG. 16 may be implemented by the gaining instruction acquisition sub-module 312. As shown in FIG. 16, a process 1600 for obtaining a gain value of ultrasonic echo signal may include one or more of the following operations.

In 1610, at least one medium propagation time corresponding to at least one depth value of the target object may be determined based on the effective aperture corresponding to the emission of the ultrasonic wave and the at least one depth value.

After the ultrasonic beams reaches the outer surface of the target object or a portion of the target object, the ultrasonic beams may continue to propagate inside the target object or a portion of the target object, and return different ultrasonic echo signals from different positions inside the target object or a portion of the target object.

At least one depth value of the target object may be a distance between at least one position point inside the target object or a portion of the target object and the transducer in a direction of the longitudinal axis.

The medium propagation time may be a time when the ultrasonic wave is transmitted from the effective array element (i.e., the effective aperture) to the reception array element. In some embodiments, the at least one medium propagation time may include at least one emission time and/or at least one ultrasonic echo time.

The emission time may be a time when the ultrasonic wave is emitted from the effective array element (i.e., the effective aperture) to a certain position inside the target object or a portion of the target object. In some embodiments, the emission time may be obtained based on the time of the ultrasonic wave being from the focus to a certain position inside the target object or a portion of the target object, and the time of the ultrasonic wave being from the focus to the center array element of the effective array element.

Figure 19:
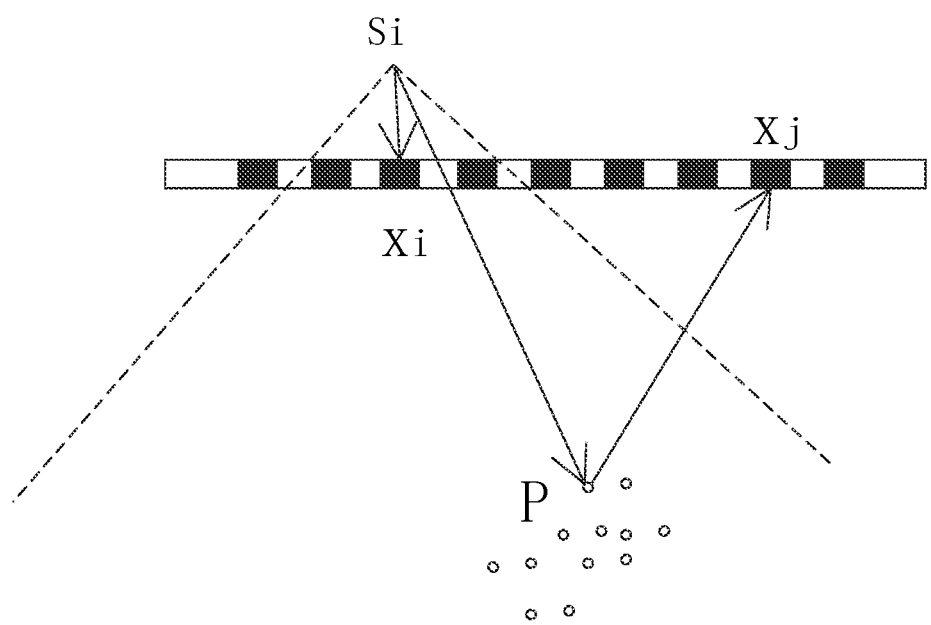
FIG. 19 is a schematic diagram illustrating emitting an ultrasonic wave based on an effective aperture according to some embodiments of the present disclosure.

As shown in FIG. 19, Si is a focus corresponding to an emission, Xi is a center array element of the effective array element corresponding to the emission, point P is a position inside the target object, and the emission time may be a time difference between the time that the ultrasonic wave is from the focus Si to the point P inside the target object and the time that the ultrasonic wave is from the focus Si to the center array element Xi.

The ultrasonic echo time may be a time when the ultrasonic echo signal reaches the reception array element from a certain position inside the target object or a portion of the target object. The reception array element may be an array element that receives ultrasonic echo signal on the transducer. In some embodiments, the gaining instruction acquisition sub-module 312 may determine the position of the reception array element based on a reflection law, the position of the center array element of the effective aperture and/or an internal position of the target object or a portion of the target object corresponding to the ultrasonic echo signal.

As shown in FIG. 19, Xj is a reception array element that receives the ultrasonic echo signal returned from point P inside the target object. The position of the reception array element Xj and the center array element Xi may be symmetrical to point P in the direction of the longitudinal axis, and the corresponding ultrasonic echo time may be the time when the ultrasonic echo signal reaches the reception array element Xi from point P inside the target object.

In some embodiments, the gaining instruction acquisition sub-module 312 may determine the medium propagation time t based on Equation (18):

$$t = \frac{1}{c}(|S_iP| + |PX_j| - |S_iX_i|) \tag{18}$$

where $|S_iX_i|$ is a distance from the focus Si to the center array element of the effective aperture, which may be obtained based on a coordinate of the focus position and the effective aperture. For example, a coordinate of the focus position is $(x_{si}, z_{si})$, a coordinate of the center array element Xi of the effective aperture is $(x_i, 0)$, then $|S_iX_i|$ is equal to $|z_{si}|$. $|S_iP|$ is a distance from the focus Si to the point P inside the target object, which may be obtained based on the focus position and a position of the point P; $|PX_j|$ is a distance from the point P inside the target object to the reception array element Xj, which may be obtained based on a position of the reception array element Xj and the position of the point P; c is a propagation speed of ultrasonic waves.

In 1620, at least one gain value corresponding to the at least one depth value may be determined based on an attenuation index of ultrasonic propagation, a noise value and the at least one medium propagation time.

Figure 17A:
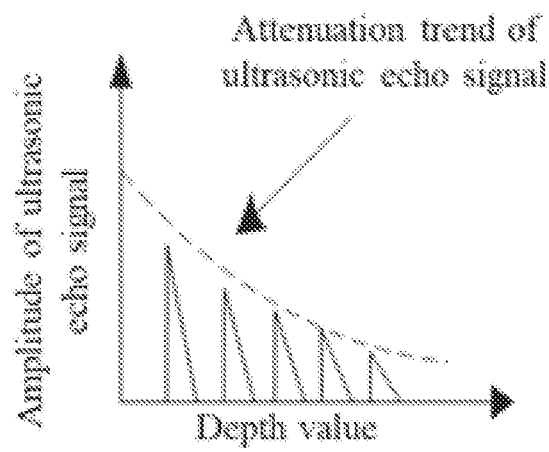
FIG. 17a is a schematic diagram illustrating an exemplary curve of relationship of a depth value and attenuation trend of ultrasonic echo signal according to some embodiments of the present disclosure.
Figure 17B:
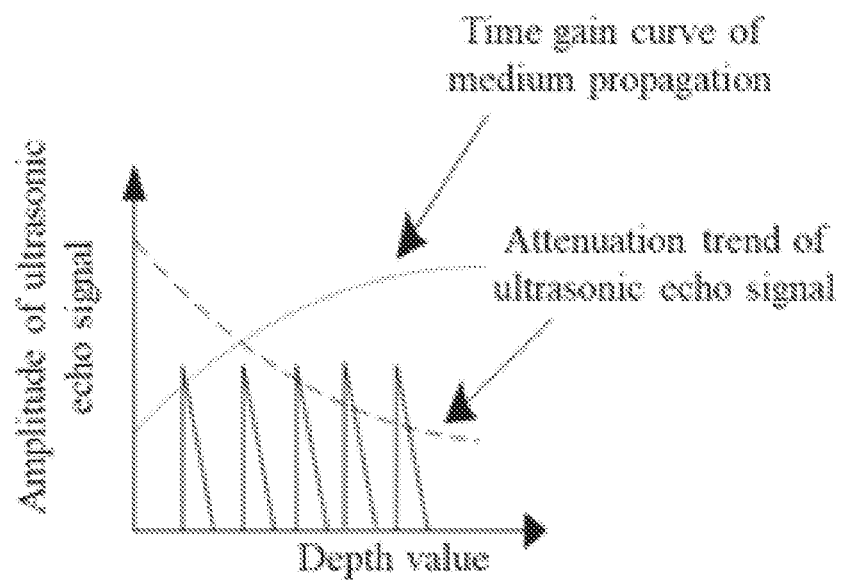
FIG. 17b is a schematic diagram illustrating an exemplary curve of relationship of a gain value and a depth value according to some embodiments of the present disclosure.

The attenuation index of ultrasonic propagation may be a parameter related to energy attenuation of ultrasonic propagation. As shown in FIG. 17, the greater the corresponding depth value of the target object or a portion of the target object is, the longer the corresponding medium propagation time is, the more the energy loses in a propagation process of the ultrasonic waves, and the ultrasonic echo signal may show an attenuation trend.

The noise may be interference information in the ultrasonic echo signal. The noise value may be a noise intensity in the ultrasonic echo signal. In some embodiments, the noise value may be a fixed value.

In some embodiments, in an ideal state without noise, the gaining instruction acquisition sub-module 312 may obtain an intensity of the ultrasonic echo signal based on the medium propagation time through Equation (19):

$$S(t) = S(0)e^{at} \tag{19}$$

where S(t) represents the intensity of the ultrasonic echo signal related to medium propagation time in the ideal state, S(0) represents an intensity of an initial ultrasonic echo signal when the medium propagation time t=0 (i.e., the depth value is 0), α is an attenuation index of ultrasonic propagation.

As mentioned above, the noise may be the interference information in the ultrasonic echo signal. In some embodiments, the gaining instruction acquisition sub-module 312 may further obtain the intensity of the ultrasonic echo signal based on the noise value through Equation (20):

$$S(t)' = S(0)\sqrt{e^{\alpha t} + \epsilon^2} \quad (20)$$

where S(t)' represents the intensity of the ultrasonic echo signal related to medium propagation time with an influence of the noise, $\epsilon^2$ represents the noise value.

The gain value may be a parameter that amplifies the intensity of the ultrasonic echo signal received by the reception array element to the same intensity as the initial ultrasonic echo signal. In some embodiments, the gaining instruction acquisition sub-module 312 may designate the intensity S(0) of the initial ultrasonic echo signal as an amplified reference and obtain the gain value corresponding to the depth value through Equation (21):

$$\Gamma(t) = \frac{s(0)}{s(t)'} = \frac{1}{\sqrt{e^{\alpha t} + \varepsilon^2}} \quad (21)$$

where Γ(t) represent a gain value corresponding to the medium propagation time t, as mentioned above, the medium propagation time t may be determined based on the depth value of the target object, thus, different depth values of the target object may correspond to different gain values.

As shown in FIG. 17, the greater the depth value corresponding to the target object or a portion of the target object is (or the longer the medium propagation time is), the gain value curve determined based on the medium propagation time t may show an upward trend, so that the intensity of the ultrasonic echo signal after gaining may not be affected by different depth values.

Some embodiments of the present disclosure show that obtaining the medium propagation time based on the effective aperture, the focus position and/or the depth value of different positions, and obtaining the corresponding gain value based on the medium propagation time, which may reduce the influence of factors such as the effective aperture, the focus position and/or the depth value of different positions on the intensity of the ultrasonic echo signal after gaining based on the gain value.

Figure 18:
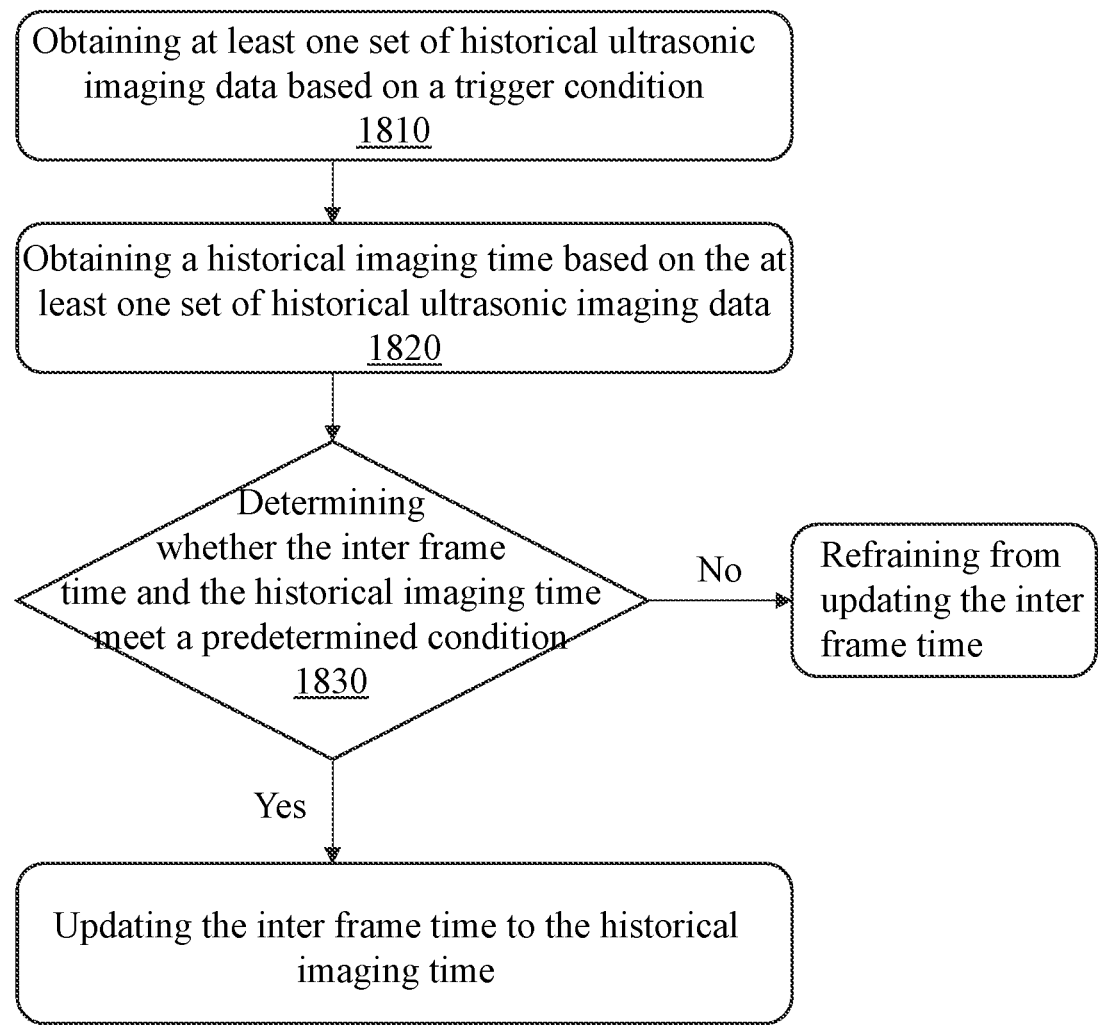
FIG. 18 is a flowchart illustrating an exemplary process for determining inter frame time according to some embodiments of the present disclosure.

FIG. 18 is a flowchart illustrating an exemplary process for determining inter frame time according to some embodiments of the present disclosure. Specifically, FIG. 18 may be implemented by the idle instruction acquisition sub-module 313.

As mentioned above, each ultrasonic image may be obtained based on the scanning data corresponding to a plurality of emissions. In some embodiments, the process of obtaining each frame of ultrasonic image may include: generating one or more emitting instructions, emitting ultrasonic waves to the target object based on the emitting instructions, receiving reflected ultrasonic waves (i.e., scanning data) from the target object, generating an initial ultrasonic image based on the reflected ultrasonic waves, and processing the initial ultrasonic image to generate an ultrasonic image. It can be seen from the operation 710 that the intra frame time is a time for emitting ultrasonic waves corresponding to each image frame, and the inter frame time is an interval time between emissions of ultrasonic waves corresponding to two adjacent image frames, which may include the time of receiving reflected ultrasonic wave (i.e., scanning data) from the target object, the time of generating initial ultrasonic image based on reflected ultrasonic wave and the time of processing initial ultrasonic image to generate the target ultrasonic image, and the time of generating the one or more emitting instructions of the next frame image.

If the inter frame time is too long, there may be a long pause time after generating an ultrasonic image and before emitting the ultrasonic waves corresponding to the next frame of ultrasonic image, resulting in a jamming of ultrasonic image(s) and reducing a generation efficiency of the ultrasonic image(s) at the same time. If the inter frame time is too short, emitting the ultrasonic waves corresponding to the next ultrasonic image before obtaining the previous ultrasonic image may cause the loss of information of the previous ultrasonic image and cause the jamming of the ultrasonic image(s). Therefore, it is necessary to determine the inter frame time to match the generation efficiency of the ultrasonic image.

As shown in FIG. 18, a process 1800 for determining the inter frame time may include one or more of the following operations.

In 1810, at least one set of historical ultrasonic imaging data may be obtained based on a trigger condition.

The historical ultrasonic imaging data may be the data obtained in a process of generating ultrasonic image. A set of historical ultrasonic imaging data may be obtained every time a frame of ultrasonic image is generated. In some embodiments, at least one set of historical ultrasonic imaging data may include at least one of ultrasonic propagation time, imaging time, and image processing time.

The ultrasonic propagation time may include the time of emitting the ultrasonic waves to the target object and/or the time of receiving the reflected ultrasonic wave from the target object. The time of emitting the ultrasonic waves to the target object may include the time of generating the one or more emitting instructions and/or the time of reaching the target object after emitting the ultrasonic waves. In some embodiments, the one or more emitting instructions may include parameters such as the pulses, focus trajectory and/or gaining of emissions. In some embodiments, the time of generating the one or more emitting instructions may be obtained from the processing device. For example, the time consumed by the CPU of the processing device to implement "generating the emitting instruction" may be counted based on an interface (such as a relevant API in Cuda time library). In some embodiments, the time of reaching the target object after emitting ultrasonic waves and the time of receiving the reflected ultrasonic wave from the target object may be obtained based on the ultrasonic probe. It should be noted that, compared with the above medium propagation time, the ultrasonic propagation time may also include the time of generating the one or more emitting instructions, but may not include the time that the ultrasonic waves transmitting from the focus to a certain position inside the target object or a portion of the target object.

The imaging time may be the time of generating the initial ultrasound image based on the reflected ultrasonic waves. In some embodiments, the imaging time may include beam synthesis time and image compose time. The beam synthesis time may be the time for synthesizing the reflected ultrasonic waves received by a plurality of array elements. The image compose time may be the time to compose the initial ultrasonic image based on the multiple images (such as multiple scanning lines) corresponding to the reflected multiple ultrasonic waves. In some embodiments, the imaging time may be obtained from the processing device. For example, the time consumed by the GPU of the processing device to implement "composing image" may be counted based on an interface (such as a relevant API in the C language time library).

The image processing time may be the time for processing the initial ultrasonic image and generating the processed ultrasonic image. More descriptions for processing the initial ultrasound image may be found in the descriptions of operation 740. In some embodiments, the image processing time may be obtained from the processing device. For example, the time consumed by the processing device to implement "spatial filtering" may be counted based on an interface (such as an API related to OpenGL).

In some embodiments, the storage device may obtain the historical ultrasonic imaging data from the processing device and the ultrasonic probe. Further, the idle instruction acquisition sub-module 313 may obtain at least one set of historical ultrasonic imaging data from the storage device based on the trigger condition.

The trigger condition may be a condition for obtaining the historical ultrasonic imaging data. In some embodiments, the trigger condition may include turning on an ultrasonic imaging system, changes of system parameters, an interval time reaching a predetermined value, or the like.

Turning on the ultrasonic imaging system may refer to turning on the ultrasonic imaging system for the first time after turning off the ultrasonic imaging system last time. In some embodiments, at least one set of historical ultrasonic imaging data may be historical ultrasonic imaging data from the last time the ultrasonic imaging system was turned on to the last time the ultrasonic imaging system was turned off. For example, during the period from the last time the ultrasonic imaging system was turned on to the last time the ultrasonic imaging system was turned off, a total of 5 ultrasonic scans were carried out, and 50 ultrasonic images were generated in each of 5 ultrasonic scans, then the idle instruction acquisition sub-module 313 may "turn on the ultrasonic imaging system" based on the trigger condition and obtain 50 sets of historical ultrasonic imaging data from the storage device.

The changes of system parameters may mean that the changes of values of specific parameters to meet predetermined requirements. For example, the changes of the system parameters may be changes of the ultrasonic examination mode. For example, the ultrasonic examination mode may change from belly examination mode to vascular examination mode. As another example, the changes of the system parameters may be changes in the value of a specific parameter that exceeds a threshold. For example, changes of a count of emission times corresponding to each ultrasonic image may exceed more than 10%. As another example, changes of the system parameters may be that a count of changed feature parameters reaches a threshold. For example, when the count of changed feature parameters exceeds 10. In some embodiments, the at least one set of historical ultrasonic imaging data may be historical ultrasonic imaging data from the last system parameter change to the current system parameter. For example, the ultrasonic examination mode is changed from the belly examination mode to the vascular examination mode, and the at least one set of historical ultrasonic imaging data may include historical ultrasonic imaging data stored during the belly examination mode.

The interval time reaching a predetermined value may mean that the interval time between the current time and the last time to obtain the at least one set of historical ultrasonic imaging data is equal to a predetermined time. For example, the predetermined time is 24 hours, and the last time to obtain the at least one set of historical ultrasonic imaging data is 8:00 on Jan. 1, 2021, so the current time is 8:00 on Jan. 2, 2021, and the interval time is 24 hours, that is, the trigger condition is met. In some embodiments, at least one set of historical ultrasonic imaging data may be historical ultrasonic imaging data within the interval time. Continuing with the above example, the idle instruction acquisition sub-module 313 may obtain the historical ultrasonic imaging data from the storage device from 8:00 on Jan. 1, 2021 to 8:00 on Jan. 2, 2021 based on "the current time is 8:00 on Jan. 2, 2021".

In 1820, a historical imaging time may be obtained based on the at least one set of historical ultrasonic imaging data.

The historical imaging time may be a time required to generate a historical ultrasound image.

Specifically, the idle instruction acquisition sub-module 313 may obtain historical imaging time corresponding to each frame of a historical ultrasonic image based on each set of historical ultrasonic imaging data.

In some embodiments, the historical imaging time corresponding to each frame of the historical ultrasonic image may be a sum of time consumed in each step in the process of generating each frame of the historical ultrasonic image, for example, a sum of ultrasonic propagation time, imaging time and/or image processing time in the process of generating each frame of the historical ultrasonic image. For example, at least one set of historical ultrasonic imaging data may include 50 sets of historical ultrasonic imaging data obtained in the process of generating 50 frames of ultrasonic image, wherein the imaging time corresponding to the first frame of the historical ultrasonic image may include a sum 30.1 s of ultrasonic propagation time 0.1 s, imaging time 10 s and image processing time 20 s in the process of generating the first frame of the historical ultrasonic image.

In some embodiments, the imaging time corresponding to each frame of the historical ultrasound image may also be a weighted sum of time consumed at each step in the process of generating each frame of the historical ultrasound image. A weight corresponding to the time consumed in each step may be determined based on a predicted growth rate of the time consumed in each step. For example, weights corresponding to ultrasonic propagation time, imaging time and image processing time can be 1, 1.1 and 1.2 respectively, and the imaging time corresponding to the first frame of the historical ultrasonic image may be 0.1×1+10×1.1+20×1.2=35.1 s.

Further, the idle instruction acquisition sub-module 313 may obtain the historical imaging time based on the imaging time corresponding to each frame of the historical ultrasound image.

In some embodiments, the historical imaging time may be an average of the imaging time of at least one frame of the historical ultrasonic image corresponding to at least one set of ultrasonic imaging historical data. Continuing with the above example, if the imaging time corresponding to the first frame of the historical ultrasonic image, the imaging time corresponding to the second frame of the historical ultrasonic image, the imaging time corresponding to the third frame of the historical ultrasonic image, . . . , the imaging time corresponding to the $50^{th}$ frame of the historical ultrasound image is 35.1 s, 34.9 s, 35 s, . . . , 34 respectively, the historical imaging time may be (35.1+34.9+35+ . . . +34)/50=355.

Some embodiments of the present disclosure show that directly designating the average of the imaging time of a plurality of frames of the historical ultrasonic image as the historical imaging time, which may improve the operation efficiency. The "50 frames" used in the present disclosure are only used to describe specific exemplary embodiments and do not limit the scope of the present disclosure.

In some embodiments, the idle instruction acquisition sub-module 313 may further set a weight for the imaging time of at least one frame of the historical ultrasonic image based on the time. For example, the idle instruction acquisition sub-module 313 may set linear growth weights with a total of 1 for 50 frames of the ultrasonic images arranged in a chronological order as: 0, 0.0008, 0.0016, . . . , 0.0384, 0.0392, 0.04, then the historical imaging time may be 35.1×0+34.9×0.0008+35×0.0016+ . . . +34×0.04=35 s.

Some embodiments of the present disclosure show that setting weights for the corresponding imaging time based on a generation order of each frame of the historical ultrasonic image. The closer the historical ultrasonic image is to the current time, the higher the corresponding imaging time weight is, so that the value of the historical imaging time is closer to the time required to generate one frame of ultrasonic image.

In 1830, whether the inter frame time and the historical imaging time meet a predetermined condition may be determined.

As mentioned above, the inter frame time is the interval time between emissions of ultrasonic waves corresponding to two adjacent image frames, which may include the time of receiving the reflected ultrasonic waves (i.e., scanning data) corresponding to the previous frame image from the target object, the time of generating a previous frame of the initial ultrasound image based on the reflected ultrasonic, and/or the time of processing the previous frame of the initial ultrasound image to generate the previous frame of the target ultrasonic image, and the time of generating the emitting instructions of the next frame image.

The determined condition may be a condition for updating the inter frame time. In some embodiments, the predetermined condition may be that a difference between the historical imaging time and the inter frame time exceeds a time threshold. For example, the difference between the historical imaging time and the inter frame time exceeds the time threshold 1 s. In some embodiments, the predetermined condition may also be that a difference ratio between the historical imaging time and the inter frame time exceeds a percentage threshold. For example, the difference ratio between the historical imaging time and the inter frame time exceeds the percentage threshold 20%.

Further, if the inter frame time and the historical imaging time meet the predetermined condition, the inter frame time may be updated to the historical imaging time. For example, the current inter frame time is 3 s, the historical imaging time is 2 s, and the difference ratio between the historical imaging time and the inter frame time is (3−2)/3×100%=33.3%, which exceeds the percentage threshold 20%, the inter frame time may be updated to 2 s. If the inter frame time and historical imaging time do not meet the predetermined conditions, the inter frame time may be refrained from updating. For example, the current inter frame time is 3 s, the historical imaging time is 2.5 s, and the difference ratio between the historical imaging time and the inter frame time is (3−2.5)/×100%=16.7%, which is less than the percentage threshold 20%, the inter frame time may be refrained from updating, that is, the inter frame time is still 3 s.

Some embodiments of the present disclosure show that adjusting the inter frame time by comparing the inter frame time and the historical imaging time. Specifically, when the difference between the inter frame time and the historical imaging time is large, that is, when an adaptability of the inter frame time and the system is poor, the inter frame time may be adjusted. On the contrary, the inter frame time may not be adjusted, so that the inter frame time may change dynamically with changes of the system performance, to obtain high-quality ultrasonic images.

The possible beneficial effects of the embodiment of the present disclosure include but are not limited to: (1) storing the one or more emitting instructions, the one or more gaining instructions, the one or more receiving instructions and the one or more idle instructions directly in any position in the ring buffer in any order, and taking out these instructions from the ring buffer for execution based on a corresponding storage position respectively, which may avoid frequent memory allocation and release, reduce system overhead and memory fragments, and improve the operation efficiency of the system; (2) mapping the plurality of first relative positions distributed at equal intervals to a plurality of second relative positions distributed at unequal intervals corresponding to the plurality of emissions based on a curve, and designing the focus trajectory of emitting the ultrasonic waves with dense focuses on both sides based on the plurality of second relative positions distributed at unequal intervals and the curvature of the transducer, which may compensate for the low resolution of the edge of ultrasonic image caused by the energy loss on both sides of the ultrasonic probe, at the same time, the focus trajectory of emitting the ultrasonic waves with dense middle focuses may be designed for the convex array ultrasonic probe, to improve the ultrasonic image resolution of the target object in the deep position; (3) determining the effective array element (or effective aperture) based on the array element directivity may improve the influence of acoustic grating lobe and reduce the energy loss of ultrasonic in the emission process, so as to improve the image quality of ultrasonic image; (4) dividing the pulses into transmission groups based on the transmission efficiency for compressing and transmitting, which may improve the transmission efficiency based on different bandwidth, so as to improve the efficiency of ultrasonic imaging; (5) based on the effective aperture, the focus position and the depth value of different positions, obtaining the medium propagation time, and obtaining the corresponding gain value based on the medium propagation time, which may reduce the effective aperture, the focus position and the depth value of different positions on the intensity of the ultrasonic echo signal after gaining based on the gain value; (6) based on the historical ultrasonic imaging data, the inter frame time may be dynamically adjusted, so that the inter frame time may change dynamically with changes of system performance, so as to obtain high-quality ultrasonic images. It should be noted that different embodiments may produce different beneficial effects. In different embodiments, the possible beneficial effects can be any one or a combination of the above, or any other possible beneficial effects.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Meanwhile, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as an "data block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Contents of each of patents, patent applications, publications of patent applications, and other materials, such as articles, books, specifications, publications, documents, etc., referenced herein are hereby incorporated by reference, excepting any prosecution file history that is inconsistent with or in conflict with the present document, or any file (now or later associated with the present disclosure) that may have a limiting effect to the broadest scope of the claims. It should be noted that if the description, definition, and/or terms used in the appended materials of the present disclosure is inconsistent or conflicts with the content described in the present disclosure, the use of the description, definition and/or terms of the present disclosure shall prevail.

Finally, it should be understood that the embodiments described in the present disclosure merely illustrates the principles of the embodiments of the present disclosure. Other modifications may be within the scope of the present disclosure. Accordingly, by way of example, and not limitation, alternative configurations of embodiments of the present disclosure may be considered to be consistent with the teachings of the present disclosure. Accordingly, the embodiments of the present disclosure are not limited to the embodiments explicitly introduced and described by the present disclosure.

What is claimed is:

1. An ultrasonic imaging method for scanning a target object using an ultrasonic probe, implemented by at least one processor when the at least one processor executes computer readable program code stored in at least one computer readable medium, the method comprising:
    obtaining a radius of a transducer of the ultrasonic probe, an array element width of the transducer, and a focus position of an ultrasonic wave to be emitted by the transducer toward the target object, the transducer including array elements configured for ultrasonic wave emission and image data collection;
    determining whether there is an invalid array element among the array elements of the transducer corresponding to an emission of the ultrasonic wave based on the radius of the transducer, the array element width, and the focus position, the invalid array element being an array element that ultrasonic beams emitted by the array element are unable to reach the target object;
    in response to an existence of the invalid array element in the emission of the ultrasonic wave, determining one or more effective array elements corresponding to the emission of the ultrasonic wave among the array elements of the transducer based on the radius of the transducer, the array element width and the focus position corresponding to the emission of the ultrasonic wave, each effective array element being an array element that ultrasonic beams emitted by the array element are able to reach the target object; or in response to an absence of the invalid array element in the emission of the ultrasonic wave, determining all array elements of the transducer as the one or more effective array elements;
    exciting the one or more effective array elements corresponding to the emission of the ultrasonic wave to emit the ultrasonic wave toward the target object;
    obtaining ultrasonic image information collected by the transducer after the ultrasonic wave is emitted to the target object; and
    generating a target ultrasonic image of the target object based on the ultrasonic image information.

2. The method of claim 1, wherein the determining whether there is an invalid array element among the array elements of the transducer corresponding to the emission of the ultrasonic wave based on the radius of the transducer, the array element width, and the focus position includes:
    determining a maximum value of an array element pointing angle corresponding to the emission of the ultrasonic wave based on the array element width;
    determining a maximum pointing circle corresponding to the maximum value of the array element pointing angle based on the radius of the transducer and the maximum value of the array element pointing angle;
    determining whether the focus position is within the maximum pointing circle;
    in response to a determination that the focus position is within the maximum pointing circle, determining that there is no invalid array element in the emission of the ultrasonic wave; and
    in response to a determination that the focus position is not within the maximum pointing circle, determining that there is an invalid array element in the emission of the ultrasonic wave.

3. The method of claim 2, wherein the determining one or more effective array elements corresponding to the emission of the ultrasonic wave based on the radius of the transducer, the array element width and the focus position corresponding to the emission of the ultrasonic wave includes:
    determining a first deflection angle based on the radius of the transducer and the focus position, wherein the first deflection angle is an angle between a connecting line of a center of the transducer and the focus position and a central axis of the transducer;
    determining a second deflection angle based on the maximum pointing circle, the radius of the transducer and the focus position, wherein the second deflection angle is an angle between the connecting line of the center of the transducer and the focus position and a tangent of the maximum pointing circle passing through the focus position;
    determining a first slope of a first connecting line between the focus position and an initial left boundary effective array element based on a difference between the first deflection angle and the second deflection angle;
    determining a second slope of a second connecting line between the focus position and an initial right boundary effective array element based on a sum of the first deflection angle and the second deflection angle; and
    obtaining a left boundary effective array element and a right boundary effective array element based on the first slope, the second slope, the radius of the transducer and a boundary of all array elements, to determine the one or more effective array elements corresponding to the emission of the ultrasonic wave.

4. The method of claim 3, wherein the obtaining a left boundary effective array element and a right boundary effective array element based on the first slope, the second slope, the radius of the transducer and the boundary of all array elements includes:
    determining a position of the initial left boundary effective array element and a position of the initial right boundary effective array element based on the first slope, the second slope and the radius of the transducer, wherein the position of the initial left boundary effective array element and the position of the initial right boundary effective array element meet an array element directivity restriction condition;
    in response to a determination that the position of the initial left boundary effective array element and/or the position of the initial right boundary effective array element are within the boundary of all array elements, designating the initial left boundary effective array element and/or the initial right boundary effective array element as the left boundary effective array element and/or the right boundary effective array element, respectively; and
    in response to a determination that the position of the initial left boundary effective array element and/or the position of the initial right boundary effective array element is not within the boundary of all array elements, designating one or more array elements at the boundary of all array elements as the left boundary effective array element and/or the right boundary effective array element.

5. The method of claim 1, wherein the exciting the one or more effective array elements corresponding to the emission of the ultrasonic wave to emit the ultrasonic wave toward the target object includes:
- determining an amplitude and/or a direction of an electrical signal that excites the one or more effective array elements corresponding to the emission based on a pulse of the ultrasonic wave according to one or more emitting instructions; and
- using the electrical signal to excite the one or more effective array elements corresponding to the emission according to the one or more emitting instructions to emit the ultrasonic wave.

6. The method of claim 1, wherein the exciting the one or more effective array elements corresponding to the emission of the ultrasonic wave includes:
- storing an emitting instruction, a gaining instruction, a receiving instruction, and an idle instruction relating to the ultrasonic wave into a ring buffer, wherein the emitting instruction at least includes the one or more effective array elements corresponding to the emission of the ultrasonic wave;
- obtaining the emitting instruction of the ultrasonic wave from the ring buffer;
- exciting the one or more effective array elements corresponding to the emission of the ultrasonic wave to emit the ultrasonic wave according to the emitting instruction.

7. The method of claim 6, further comprising:
- determining at least one medium propagation time corresponding to at least one depth value of the target object based on the one or more effective array elements corresponding to the emission of the ultrasonic wave and the at least one depth value, wherein the at least one medium propagation time includes at least one emission time and at least one ultrasonic echo time, and the at least one depth value is a distance between at least one position point inside the target object and the transducer in a longitudinal axis direction; and
- determining at least one gain value corresponding to the at least one depth value based on an attenuation index of ultrasonic propagation, a noise value and the at least one medium propagation time.

8. The method of claim 7, the obtaining ultrasonic image information further comprising:
- obtaining the gaining instruction, the receiving instruction, and the idle instruction relating to the ultrasonic wave from the ring buffer;
- obtaining at least one initial echo signal corresponding to the emission of the ultrasonic wave collected by one or more reception array elements of the transducer specified in the receiving instruction;
- performing an analog gain operation on the at least one initial echo signal corresponding to the emission of the ultrasonic wave based on the gaining instruction to obtain at least one enhanced echo signal; and
- processing the at least one enhanced echo signal based on the idle instruction to obtain the ultrasonic image information corresponding to the emission of the ultrasonic wave.

9. The method of claim 8, the generating a target ultrasonic image of the target object further comprising:
- composing the ultrasonic image information to obtain an initial ultrasonic image;
- performing a digital gain operation on the initial ultrasonic image based on the at least one gain value; and
- processing the initial ultrasonic image after gaining to obtain the target ultrasonic image, wherein the processing the initial ultrasonic image after gaining includes at least one of spatial filtering, image rendering, image compression or scanning conversion.

10. The method of claim 2, wherein the ultrasonic probe is a convex array ultrasonic probe, the array element pointing angle including angles corresponding to the array elements, an angle corresponding to an array element being an angle between a first connection line and a second connection line, the first connection line connecting a center of the transducer and the array element, the second connection line connecting the focus position and the array element.

11. The method of claim 10, wherein the center of the transducer is the center of the maximum pointing circle, and the radius of the maximum pointing circle is a product of a sine value of the maximum value of the array element pointing angle and the radius of the transducer.

12. The method of claim 11, wherein the determining whether the focus position is within the maximum pointing circle comprises:
- determining a distance from the focus position to the center of the maximum pointing circle;
- determining whether the distance is smaller than or equal to the radius of the maximum point circle;
- in response to determining that the distance is smaller than or equal to the radius of the maximum point circle, determining that the focus position is within the maximum pointing circle.

13. An ultrasonic imaging system, comprising:
- at least one computer readable medium including computer readable program code;
- at least one processor configured to communicate with the at least one computer readable medium, wherein when executing the computer readable program code, the at least one processor is configured to perform operations comprising:
- obtaining a radius of a transducer of the ultrasonic probe, an array element width of the transducer, and a focus position of an ultrasonic wave to be emitted by the transducer toward the target object, the transducer including array elements configured for ultrasonic wave emission and image data collection;
- determining whether there is an invalid array element among the array elements of the transducer corresponding to an emission of the ultrasonic wave based on the radius of the transducer, the array element width, and the focus position, the invalid array element being an array element that ultrasonic beams emitted by the array element are unable to reach the target object;
- in response to an existence of the invalid array element in the emission of the ultrasonic wave, determining one or more effective array elements corresponding to the emission of the ultrasonic wave among the array elements of the transducer based on the radius of the transducer, the array element width and the focus position corresponding to the emission of the ultrasonic wave, each effective array element being an array element that ultrasonic beams emitted by the array element are able to reach the target object; or in response to an absence of the invalid array element in the emission of the ultrasonic wave, determining all array elements of the transducer as the one or more effective array elements;
- exciting the one or more effective array elements corresponding to the emission of the ultrasonic wave to emit the ultrasonic wave toward the target object;

obtaining ultrasonic image information collected by the transducer after the ultrasonic wave is emitted to the target object; and generating a target ultrasonic image of the target object based on the ultrasonic image information.

14. The system of claim 13, wherein the determining whether there is an invalid array element among the array elements of the transducer corresponding to the emission of the ultrasonic wave based on the radius of the transducer, the array element width, and the focus position includes:

determining a maximum value of an array element pointing angle corresponding to the emission of the ultrasonic wave based on the array element width;

determining a maximum pointing circle corresponding to the maximum value of the array element pointing angle based on the radius of the transducer and the maximum value of the array element pointing angle;

determining whether the focus position is within the maximum pointing circle;

in response to a determination that the focus position is within the maximum pointing circle, determining that there is no invalid array element in the emission of the ultrasonic wave; and in response to a determination that the focus position is not within the maximum pointing circle, determining that there is an invalid array element in the emission of the ultrasonic wave.

15. The system of claim 14, wherein the determining one or more effective array elements corresponding to the emission of the ultrasonic wave based on the radius of the transducer, the array element width and the focus position corresponding to the emission of the ultrasonic wave includes:

determining a first deflection angle based on the radius of the transducer and the focus position, wherein the first deflection angle is an angle between a connecting line of a center of the transducer and the focus position and a central axis of the transducer;

determining a second deflection angle based on the maximum pointing circle, the radius of the transducer and the focus position, wherein the second deflection angle is an angle between the connecting line of the center of the transducer and the focus position and a tangent of the maximum pointing circle passing through the focus position;

determining a first slope of a first connecting line between the focus position and an initial left boundary effective array element based on a difference between the first deflection angle and the second deflection angle;

determining a second slope of a second connecting line between the focus position and an initial right boundary effective array element based on a sum of the first deflection angle and the second deflection angle; and obtaining a left boundary effective array element and a right boundary effective array element based on the first slope, the second slope, the radius of the transducer and a boundary of all array elements, to determine the one or more effective array elements corresponding to the emission of the ultrasonic wave.

16. The system of claim 15, wherein the obtaining a left boundary effective array element and a right boundary effective array element based on the first slope, the second slope, the radius of the transducer and the boundary of all array elements includes:

determining a position of the initial left boundary effective array element and a position of the initial right boundary effective array element based on the first slope, the second slope and the radius of the transducer, wherein the position of the initial left boundary effective array element and the position of the initial right boundary effective array element meet an array element directivity restriction condition;

in response to a determination that the position of the initial left boundary effective array element and/or the position of the initial right boundary effective array element are within the boundary of all array elements, designating the initial left boundary effective array element and/or the initial right boundary effective array element as the left boundary effective array element and/or the right boundary effective array element, respectively; and in response to a determination that the position of the initial left boundary effective array element and/or the position of the initial right boundary effective array element is not within the boundary of all array elements, designating one or more array elements at the boundary of all array elements as the left boundary effective array element and/or the right boundary effective array element.

17. The system of claim 13, wherein the exciting the one or more effective array elements corresponding to the emission of the ultrasonic wave to emit the ultrasonic wave toward the target object includes:

determining an amplitude and/or a direction of an electrical signal that excites the one or more effective array elements corresponding to the emission based on a pulse of the ultrasonic wave according to one or more emitting instructions; and using the electrical signal to excite the one or more effective array elements corresponding to the emission according to the one or more emitting instructions to emit the ultrasonic wave.

18. The system of claim 13, wherein the exciting the one or more effective array elements corresponding to the emission of the ultrasonic wave includes:

storing an emitting instruction, a gaining instruction, a receiving instruction, and an idle instruction relating to the ultrasonic wave into a ring buffer, wherein the emitting instruction at least includes the one or more effective array elements corresponding to the emission of the ultrasonic wave;

obtaining the emitting instruction of the ultrasonic wave from the ring buffer;

exciting the one or more effective array elements corresponding to the emission of the ultrasonic wave to emit the ultrasonic wave according to the emitting instruction.

19. The system of claim 18, the operations further comprising:

determining at least one medium propagation time corresponding to at least one depth value of the target object based on the one or more effective array elements corresponding to the emission of the ultrasonic wave and the at least one depth value, wherein the at least one medium propagation time includes at least one emission time and at least one ultrasonic echo time, and the at least one depth value is a distance between at least one position point inside the target object and the transducer in a longitudinal axis direction; and determining at least one gain value corresponding to the at least one depth value based on an attenuation index of ultrasonic propagation, a noise value and the at least one medium propagation time.

20. A non-transitory computer readable medium, comprising computer readable program code, wherein when executed by at least one processor, the computer readable program code directs the at least one processor to effectuate a method, the method comprising:

obtaining a radius of a transducer of the ultrasonic probe, an array element width of the transducer, and a focus position of an ultrasonic wave to be emitted by the transducer toward the target object, the transducer including array elements configured for ultrasonic wave emission and image data collection;

determining whether there is an invalid array element among the array elements of the transducer corresponding to an emission of the ultrasonic wave based on the radius of the transducer, the array element width, and the focus position, the invalid array element being an array element that ultrasonic beams emitted by the array element are unable to reach the target object;

in response to an existence of the invalid array element in the emission of the ultrasonic wave, determining one or more effective array elements corresponding to the emission of the ultrasonic wave among the array elements of the transducer based on the radius of the transducer, the array element width and the focus position corresponding to the emission of the ultrasonic wave, each effective array element being an array element that ultrasonic beams emitted by the array element are able to reach the target object; or in response to an absence of the invalid array element in the emission of the ultrasonic wave, determining all array elements of the transducer as the one or more effective array elements;

exciting the one or more effective array elements corresponding to the emission of the ultrasonic wave to emit the ultrasonic wave toward the target object;

obtaining ultrasonic image information collected by the transducer after the ultrasonic wave is emitted to the target object; and generating a target ultrasonic image of the target object based on the ultrasonic image information.

\* \* \* \* \*